(12) United States Patent
Waysbeyn et al.

(10) Patent No.: US 8,721,710 B2
(45) Date of Patent: May 13, 2014

(54) ANASTOMOSIS SYSTEM AND METHOD

(75) Inventors: Igor Waysbeyn, Haifa (IL); Irina Vaysbeyn, Haifa (IL)

(73) Assignee: HDH Medical Ltd., Haifa, IL (US)

( * ) Notice: Subject to any disclaimer, the term of this patent is extended or adjusted under 35 U.S.C. 154(b) by 809 days.

(21) Appl. No.: 10/828,668

(22) Filed: Apr. 21, 2004

(65) Prior Publication Data

US 2005/0038502 A1 Feb. 17, 2005

Related U.S. Application Data

(60) Provisional application No. 60/493,764, filed on Aug. 11, 2003.

(51) Int. Cl.
*A61B 17/08* (2006.01)
*A61F 2/06* (2013.01)

(52) U.S. Cl.
CPC .................................... *A61F 2/064* (2013.01)
USPC ....... 623/1.36; 623/1.14; 623/1.35; 623/1.31; 606/151; 606/153

(58) Field of Classification Search
CPC ..................................................... A61F 2/064
USPC ............. 623/1.14, 1.16, 1.23, 1.31, 1.3, 1.25, 623/1.28, 1.29, 1.32, 1.36, 1.35, 1.1, 1.13; 606/153, 151, 152, 154, 155, 156, 108; 604/8
See application file for complete search history.

(56) References Cited

U.S. PATENT DOCUMENTS

| 4,368,736 A | * | 1/1983 | Kaster | 606/153 |
| 4,562,596 A | | 1/1986 | Kornberg | |
| 4,787,899 A | | 11/1988 | Lazarus | 623/1 |

(Continued)

FOREIGN PATENT DOCUMENTS

| WO | WO-95/12368 | 5/1995 | |
| WO | WO 02/17797 A1 | 8/2001 | 606/153 |

(Continued)

OTHER PUBLICATIONS

In the U.S. Patent and Trademark Office, Office Action in re: U.S. Appl. No. 12/217,642, dated Oct. 7, 2011, 12 pages.

(Continued)

*Primary Examiner* — Thomas J Sweet
*Assistant Examiner* — Cheryl Miller
(74) *Attorney, Agent, or Firm* — Venable LLP; Michele V. Frank, Esq.

(57) ABSTRACT

The present invention provides docking heads to be mounted on a graft so as to establish a vascular device that is coupled to a blood vessel with aneurysm, and dedicated delivery devices as well as methods of coupling. The vascular device comprises a graft having docking head at the proximal portion and another docking head at its distal portion, or two docking heads if the graft is bifurcated. The docking heads comprises a hollow truncated cone having a passage adapted to correspond the outer diameter of the graft and is provided with a plurality of outwardly pointing and inclined barbs. The vascular device is coupled to the blood vessel on both sides of the aneurysm while the docking heads act as guiding, anchoring and sealing means in a suture-less and rapid manner. The vascular device is modular and can be prepared according to the condition of the aneurysm and the dimensions of the blood vessels during operation.

27 Claims, 21 Drawing Sheets

(56) References Cited

U.S. PATENT DOCUMENTS

| | | | | |
|---|---|---|---|---|
| 5,042,707 | A | 8/1991 | Taheri | 606/213 |
| 5,234,447 | A * | 8/1993 | Kaster et al. | 606/153 |
| 5,452,733 | A | 9/1995 | Sterman et al. | 128/898 |
| 5,735,290 | A | 4/1998 | Sterman et al. | 128/898 |
| 5,800,521 | A | 9/1998 | Orth | |
| 5,875,782 | A | 3/1999 | Ferrari et al. | |
| 5,989,287 | A * | 11/1999 | Yang et al. | 623/1.36 |
| 6,015,431 | A * | 1/2000 | Thornton et al. | 623/1.14 |
| 6,110,198 | A * | 8/2000 | Fogarty et al. | 623/1.12 |
| 6,176,864 | B1 * | 1/2001 | Chapman | 606/153 |
| 6,190,353 | B1 | 2/2001 | Makower et al. | |
| 6,217,548 | B1 | 4/2001 | Tsugita et al. | |
| 6,290,731 | B1 | 9/2001 | Solovay et al. | 623/51.16 |
| 6,344,038 | B1 | 2/2002 | Weber | |
| 6,361,559 | B1 * | 3/2002 | Houser et al. | 623/1.36 |
| 6,409,756 | B1 | 6/2002 | Murphy | 250/623 |
| 6,447,539 | B1 * | 9/2002 | Nelson et al. | 623/1.11 |
| 6,524,335 | B1 | 2/2003 | Hartley et al. | |
| 6,635,066 | B2 * | 10/2003 | Tanner et al. | 606/151 |
| 6,656,214 | B1 * | 12/2003 | Fogarty et al. | 623/1.13 |
| 6,729,356 | B1 * | 5/2004 | Baker et al. | 139/387 R |
| 6,911,035 | B1 * | 6/2005 | Blomme | 606/153 |
| 2001/0047153 | A1 | 11/2001 | Trocki et al. | |
| 2002/0002395 | A1 * | 1/2002 | Berg et al. | 623/1.4 |
| 2002/0058993 | A1 | 5/2002 | Landau et al. | |
| 2002/0082554 | A1 | 6/2002 | Lenarz et al. | |
| 2002/0091439 | A1 * | 7/2002 | Baker et al. | 623/1.36 |
| 2002/0099394 | A1 | 7/2002 | Houser et al. | |
| 2002/0151913 | A1 * | 10/2002 | Berg et al. | 606/153 |
| 2002/0183769 | A1 | 12/2002 | Swanson et al. | |
| 2003/0019877 | A1 | 1/2003 | Scarabelli et al. | |
| 2003/0033005 | A1 | 2/2003 | Houser et al. | 623/1.35 |
| 2003/0040792 | A1 | 2/2003 | Gabbay | |
| 2003/0074007 | A1 | 4/2003 | Rosengart | |
| 2003/0074055 | A1 * | 4/2003 | Haverkost | 623/1.16 |
| 2003/0083679 | A1 | 5/2003 | Grudem et al. | |
| 2003/0093145 | A1 * | 5/2003 | Lawrence-Brown et al. | 623/1.21 |
| 2003/0130671 | A1 | 7/2003 | Duhaylongsod et al. | 606/153 |
| 2003/0130724 | A1 | 7/2003 | DePalma et al. | |
| 2003/0158575 | A1 | 8/2003 | Boylan et al. | |
| 2003/0158595 | A1 * | 8/2003 | Randall et al. | 623/1.13 |
| 2003/0167087 | A1 | 9/2003 | Piplani et al. | |
| 2003/0176877 | A1 | 9/2003 | Narciso | |
| 2003/0179877 | A1 | 9/2003 | Dezonno et al. | |
| 2003/0236567 | A1 * | 12/2003 | Elliot | 623/1.13 |
| 2004/0193245 | A1 | 9/2004 | Deem et al. | |
| 2004/0225351 | A1 * | 11/2004 | Weadock | 623/1.23 |
| 2005/0171599 | A1 * | 8/2005 | White | 623/1.36 |
| 2006/0161195 | A1 * | 7/2006 | Goldsteen et al. | 606/185 |
| 2007/0005129 | A1 * | 1/2007 | Damm et al. | 623/1.36 |
| 2009/0276032 | A1 | 11/2009 | Waysbeyn et al. | |
| 2009/0276035 | A1 | 11/2009 | Waysbeyn et al. | |

FOREIGN PATENT DOCUMENTS

| | | |
|---|---|---|
| WO | WO-01/70091 | 9/2001 |
| WO | WO-02/17797 | 3/2002 |
| WO | WO-02/34164 | 5/2002 |
| WO | WO-03/053283 | 7/2003 |
| WO | WO-2004/045459 | 6/2004 |
| WO | WO-2005/013796 | 2/2005 |

OTHER PUBLICATIONS

In the U.S. Patent and Trademark Office, Office Action in re: U.S. Appl. No. 12/217,642, dated Sep. 14, 2010, 10 pages.
In the U.S. Patent and Trademark Office, Final Office Action in re: U.S. Appl. No. 12/217,642, dated Mar. 7, 2011, 12 pages.
In the U.S. Patent and Trademark Office, Final Office Action in re: U.S. Appl. No. 12/217,651, dated Apr. 15, 2011, 11 pages.
In the U.S. Patent and Trademark Office, Office Action in re: U.S. Appl. No. 12/217,651, dated Sep. 23, 2010, 9 pages.
U.S. Appl. No. 60/493,764, filed Aug. 11, 2003, Waysbeyn et al.

* cited by examiner

ANASTOMOSIS SYSTEM AND METHOD

CROSS-REFERENCE TO RELATED APPLICATION

This application is based upon and claims the benefit of the priority filing date of commonly assigned, U.S. Provisional Patent Application Ser. No. 60/493,764, filed Aug. 11, 2003.

FIELD OF THE INVENTION

The present invention relates to devices and methods for surgically performing anastomosis of hollow organs. More particularly, the present invention relates to an artificial graft for vascular anastomosis and a method for implanting the graft in a target vessel.

BACKGROUND OF THE INVENTION

Aneurysms in the abdominal aorta are associated with particularly high mortality rates. Current medical standards call for urgent operative repair. Abdominal surgery results in substantial stress to the body, and particularly in cases of aortic aneurysm, the mortality rate is extremely high. There is also considerable mortality and morbidity associated with open surgical intervention to repair an aortic aneurysm. This intervention involves penetrating the abdominal wall to the location of the aneurysm to reinforce or replace the diseased section of the aortic aneurysm. A prosthetic device, typically a synthetic tube graft, is used for this purpose. The graft serves to exclude the aneurysm from the circulatory system, thus relieving pressure and stress on the weakened section of the aorta at the aneurysm.

Repair of an aortic aneurysm by surgical means is a major operative procedure. Substantial morbidity accompanies the procedure, resulting in a protracted recovery period. Furthermore and as mentioned herein, the procedure entails a substantial risk of mortality. While surgical intervention may be indicated and the surgery carries attendant risk, certain patients may not be able to tolerate the stress of intra-abdominal surgery. It is, therefore, desirable to reduce the mortality and morbidity associated with intra-abdominal surgical intervention.

Anastomosis is the surgical fusion of biological tissues, especially joining tubular organs to create an inter communication between them. Vascular surgery often involves producing an anastomosis between blood vessels or between a blood vessel and a vascular graft to create or restore a blood flow path to essential tissues. The first successful aortic resection for aneurysm was performed in 1951.

One anastomosis method involves harvesting a vein in the body using an artificial conduit made of Dacron or Goretex tubing, and connecting the conduit as a bypass graft from a viable artery, such as the aorta, to the coronary artery downstream of the blockage or narrowing. A graft with both the proximal and the distal ends of the graft detached is known as a "free graft".

A second method involves rerouting a less essential artery, such as the internal mammary artery, from its native location so that it may be connected to the coronary artery downstream of the blockage. The proximal end of the graft vessel remains attached in its native position.

Until about a decade ago, essentially all vascular anastomosis were performed by conventional hand suturing. Suturing the anastomosis is a time-consuming and difficult task, requiring much skill and practice on the part of the surgeon. It is important that each anastomosis provides a smooth, open flow path for the blood and that the attachment be completely leaks-proof. A completely leak-proof seal is not always achieved on the very first try. Consequently, there is a frequent need for re-suturing the anastomosis to close any leaks that are detected. The time consuming nature of hand-sutured anastomosis is disadvantageous for several reasons. First, circulatory isolation and cardiac arrest are inherently very traumatic, and it has been found that the frequency of certain post-surgical complications varies directly with the duration for which the heart is under cardioplegic arrest (frequently referred to as the "crossclamp time"). Secondly, because of the high cost of cardiac operating room time, any prolongation of the surgical procedure can significantly increase the cost of the bypass operation to the hospital and to the patient. Thus, it is desirable to reduce the duration of the cross clamp time and of the entire surgery by expediting the anastomosis procedure without reducing the quality or effectiveness of the anastomosis.

The already high degree of manual skill required for conventional manually sutured anastomosis is even more demanding for closed-chest or port-access thoracoscopic bypass surgery. A newly developed surgical procedure designed to reduce the morbidity as compared to the standard open-chest procedure described in U.S. Pat. Nos. 5,452,733 and 5,735,290. In the closed-chest procedure, surgical access to the heart is made through narrow access ports made in the intercostal spaces of the patient's chest, and the procedure is performed under thoracoscopic observation. Because the patient's chest is not opened, the suturing of the anastomosis must be performed at some distance, using elongated instruments positioned through the access ports for approximating the tissues and for holding and manipulating the needles and sutures used to make the anastomosis. This requires even greater manual skill than the already difficult procedure of suturing anastomosis during open-chest surgery.

The biggest drawback of such an anastomosis is that it requires a fair amount of mobility of the two vessel ends to allow easy and accurate placement of the sutures, and it has a tendency to be constrictive.

In order to reduce the difficulty of creating the vascular anastomosis, there was a need to provide a rapid means for making a reliable anastomosis between a bypass graft or artery and the aorta or the native vessels of the heart. A first approach to expediting and improving anastomosis procedures has been through stapling technology. Stapling technology has been successfully employed in many different areas of surgery for making tissue attachments faster and more reliably. The greatest progress in stapling technology has been in the area of gastrointestinal surgery. Various surgical stapling instruments have been developed for anastomosis of hollow or tubular organs, such as the bowel. These instruments, unfortunately, are not easily adaptable for use in creating vascular anastomosis. This is partially due to the difficulty in miniaturizing the instruments to make them suitable for smaller organs such as blood vessels. Possibly even more important is the necessity of providing a smooth, open flow path for the blood. Known gastrointestinal stapling instruments for anastomosis of tubular organs are designed to create an inverted anastomosis in which the tissue folds inward into the lumen of the organ that is being attached. This is acceptable in gastrointestinal surgery, where it is most important to approximate the outer layers of the intestinal tract. However, in vascular surgery, this geometry is unacceptable for several reasons. First, the inverted vessel walls would cause a disruption in the blood flow. This could cause decreased flow and ischemia downstream of the disruption, or, yet worse, the flow disruption or eddies could become a locus for thrombosis that could shed emboli or occlude the vessel at the anastomosis site.

Secondly, unlike the intestinal tract, the outer surfaces of the blood vessels will not grow together when approximated. The sutures, staples, or other joining device may therefore be needed permanently to maintain the structural integrity of the vascular anastomosis. Thirdly, to establish a permanent, non-thrombogenic vessel, the innermost layer should grow together for a continuous, uninterrupted lining of the entire vessel. Thus, it would be preferable to have a stapling instrument that would create vascular anastomosis that are everted, that is folded outward, or that creates direct edge-to-edge cooptation without inversion.

In recent years, methods have been developed in attempt to treat an aortic aneurysm without the attendant risks of intra-abdominal surgical intervention. For example, Komberg discloses in U.S. Pat. No. 4,562,596 "Aortic graft, device and method for performing an intraluminal abdominal aortic aneurysm repair" an aortic graft comprising a flexible tubular material having a plurality of struts along its body, to lend the graft stability and resiliency. The struts have angled hooks with barbs at their upper ends which are securely attached to the inside of the aorta above the aneurysm. Komberg's graft is inserted using a tubular device also disclosed in his patent. Komberg, however, only anchors the proximal end of the graft. Komberg claims that the downward flow of blood holds the distal graft securely in place, so that no mechanical attachment is necessary distally. The blood pressure in the abdominal aorta, however, is typically in the magnitude of 130 mm of mercury (Hg). In spite of the direction of flow of blood through the graft, proximal to distal, substantial back pressure within the aneurysm will result unless the distal end is also mechanically attached to the aorta in a manner that prevents substantial leakage of blood between the graft and the aorta. Without distal attachment, the device of Komberg will not effectively exclude the weakened arterial wall at the site of the aneurysm from the forces and stress associated with the blood pressure.

Another example can be seen in U.S. Pat. No. 4,787,899 "Intraluminal graft device, system and method", disclosed by Lazarus. Lazarus discloses a grafting system that employs a plurality of staples mounted in the proximal end of the graft. Lazarus's staples are forced through the aorta wall by means of a balloon catheter. Similarly to Komberg, Lazarus uses staples only in the proximal end of the graft. There is no teaching or suggestion as for mechanically attaching the graft to the distal aorta below the level of the aneurysm.

Taheri discloses in U.S. Pat. No. 5,042,707 "Intravascular stapler, and method of operating same" an articulatable stapler for implanting a graft in a blood vessel. The stapler is in the form of an elongated catheter with a plurality of segments mounted on the distal end of the catheter. The segments have beveled faces and are connected to each other by hinges. A wire runs through the catheter to the most distal segment. The most distal segment is moved, in conjunction with the other segments, into a firing position that is substantially perpendicular to the main catheter body by the action of pulling the wire. The staple is implanted by using two other wires that act as fingers to bend the staple into its attachment position.

Taheri, however, appears to be a single-fire design that can only implant one staple at a time. After each stapler is implanted, Taheri's design apparently requires that the catheter will be removed before another staple is loaded. In addition, Taheri does not suggest an appropriate density of staples to secure a graft against the pulsatile blood flow of the aorta. Pressures within the aorta range from 120 mm Hg pressure to 200 mm Hg pressure. Without adequate attachment, the graft may leak around the edges continuing to allow life-threatening pressures to develop in the aneurysm. Moreover, the graft can be even replaced.

Similar inherent defects as the ones referred herein are present in endovascular fastener and grafting apparatus that is disclosed in PCT application published as WO 02/17797. Moreover, it appears that some obstacles for blood flow in the vessel evolve from the wire ends. Other fasteners for the grafts are disclosed in American patent applications US 2003/0176877 by Narciso et al., US 2003/0130671 by Duhaylongsod et al and US 2003/0033005 by Houser et al.

All of the prior references require a sufficiently large section of healthy aorta surrounding the aneurysm to ensure attachment of the graft. The neck of the aorta at the end above the aneurysm is usually sufficient to maintain a graft's attachment means. However, when an aneurysm is located near the iliac arteries, there may be an ill-defined neck or no neck below the aneurysm. Such an ill-defined neck would have an insufficient amount of healthy aortic tissue to which a graft can be connected.

There are a number of shortcomings with the presently available graft products and their fixation within the abdominal aorta. Although sizing of "tube" or "bifurcated" grafts is radiographically assessed prior to surgery, it is necessary for the surgeon to have a large selection of graft lengths and diameters on hand to ensure an appropriate surgical outcome.

Additional shortcomings include the placement of a "circular" profile graft with an associated fixation device within an essentially "ovoid" profile vessel and the use of attachment means which fasten only to the insubstantial, structurally compromised (diseased) intima and media levels of the vessel wall.

Research has exposed yet another problem which indicates that the necks of the post-surgical aorta increase in size for approximately twelve months, regardless of whether the aneurysm experiences dimensional change. This phenomenon can result in perigraft leaks and graft migration Vascular endoprostheses (stent-grafts) are newly developed surgical procedure designed to reduce the drawbacks of suturing anastomosis procedure. The stents were developed about 10 years ago to avoid major conventional open surgical repair for abdominal aortic aneurysm (AAA). Parodi in 1990 performed the first human stent graft, backed by extensive animal experiments. In this method, incision is made in the patient groin and a catheter is inserted into a blood vessel that leads to the aorta. A stent graft (a Dacron tube inside a metal self expandable metal cylinder) is inserted through the catheter. Once the stent graft is in place, cylinder is expand like a spring to hold tightly against the wall of the blood vessel. Stent graft can be supplied with the ancure device (EVT/Guidant: ANCURE ENDO-HOOKS). The first production endografts to enter clinical trails in the US were approved by the FDA in September 1999 for clinical use under a careful monitored training program.

The treatment of AAA with stent grafts is rapidly evolving field. Several grafts models were introduced (U.S. Pat. Nos. 6,290,731, 6,409,756 are provided herein as references). The stent construction is unique for each type of device. Stents are working in very difficult conditions but there is no knowledge about the long-term durability. Analysis Made by G. Riepe et al. (provided herein as references) shows that the long-term durability of conventional graft is still much higher then ones of stent graft.

Hence, although in recent years certain techniques have been developed that may reduce the stress, morbidity, and risk of mortality associated with surgical intervention to repair aortic aneurysms, none of the systems that have been developed effectively treat the aneurysm and exclude the affected section of aorta from the pressures and stresses associated with circulation. None of the devices disclosed in the references to this patent application provide a reliable and quick means to reinforce an aneurismal artery.

SUMMARY OF THE INVENTION

It is an object of the present invention to provide improved system that comprises dedicated devices and methods for surgically performing anastomosis of blood vessels that may reduce mortality rate, decrease the duration of the most traumatic for patient surgical intervention, drastically shorten the circulatory isolation and discontinuance of a blood flow path to essential tissues, reduce blood losses, and decrease the vessel's trauma and the frequency of post-surgical complications.

It is another object of the present invention to provide a new and unique artificial graft for anastomosis having a docking head that reduces the complication of implantation and the high degree of manual skill that is required for conventional manually sutured anastomosis.

It is yet another object of the present invention to provide an improved method of grafting the new artificial graft so as to decrease anastomosis operation cost due to reduction in the duration of the surgical procedure.

Additionally, it is an object of the present invention to provide anastomosis devices and delivery devices so as to facilitate the placement of the anastomosis device during implantation.

It is therefore provided in accordance with a one aspect of the present invention a docking head to be mounted on a graft having an outer diameter so as to couple the graft to a blood vessel, said docking head comprising a hollow truncated cone having a passage that is adapted to correspond the outer diameter of the graft and wherein said hollow truncated cone is provided with a plurality of outwardly pointing and inclined barbs, whereby the docking head act as guiding, anchoring and sealing means in its coupling to the graft.

Furthermore, in accordance with another preferred embodiment of the present invention, said hollow truncated cone is elastic.

Furthermore, in accordance with another preferred embodiment of the present invention, said hollow truncated cone has a concaved, convex or straight profile.

Furthermore, in accordance with another preferred embodiment of the present invention, said barbs are flexible and are inclined opposite a truncated end of said hollow truncated cone.

Furthermore, in accordance with another preferred embodiment of the present invention, said barbs have a length that ranges from 1 to 4 times the thickness of a blood vessel's wall.

Furthermore, in accordance with another preferred embodiment of the present invention, said barbs are straight.

Furthermore, in accordance with another preferred embodiment of the present invention, said barbs are bent so as to establish a concave profile in respect to a radial cross section of said hollow truncated cone.

Furthermore, in accordance with another preferred embodiment of the present invention, said barbs are bent so as to establish a convex profile in respect to a radial cross section of said hollow truncated cone.

Furthermore, in accordance with another preferred embodiment of the present invention, a portion of said barbs are bent so as to establish a concave profile and another portion are bent so as to establish a convex profile in respect to a radial cross section of said hollow truncated cone.

Furthermore, in accordance with another preferred embodiment of the present invention, said hollow truncated cone is provided with a plurality of open slits adapted to allow said truncated cone to curtail its larger diameter.

In accordance with another aspect of the present invention, it is provided a vascular device for treating a blood vessel with aneurysm comprising:
  a graft having a proximal portion and a distal portion;
    at least two docking heads wherein a first docking head is provided at said proximal portion and at least one second docking head is provided at said distal portion;
    whereby the vascular device is coupled to the blood vessel on both sides of the aneurysm by said at least two docking heads that act as guiding, anchoring and sealing means in a suture-less and rapid manner.

Furthermore, in accordance with another preferred embodiment of the present invention, said graft is a tubular graft.

Furthermore, in accordance with another preferred embodiment of the present invention, said graft is a bifurcated graft.

Furthermore, in accordance with another preferred embodiment of the present invention, said graft is longer than the aneurysm and at least one of said at least two docking heads is mounted so as to move along said graft and is adapted to be fasten to a suitable positioning on said graft during treatment.

Furthermore, in accordance with another preferred embodiment of the present invention, said at least one of said at least two docking heads is coupled to said suitable positioning by a means selected from a group such as fit, glue, sutures, clips, or staples.

Furthermore, in accordance with another preferred embodiment of the present invention, said at least two docking heads have an outer diameter so as to couple the graft to the blood vessel, and wherein said at least two docking heads comprise a hollow truncated cone having a passage that is adapted to correspond an outer diameter of said graft and wherein said truncated cone is provided with a plurality of outwardly pointing and inclined barbs.

Furthermore, in accordance with another preferred embodiment of the present invention, said hollow truncated cone is elastic.

Furthermore, in accordance with another preferred embodiment of the present invention, said hollow truncated cone has a concaved, convex or straight profile adapted to a profile of said blood vessel in positioning of said at least two docking heads on said graft.

Furthermore, in accordance with another preferred embodiment of the present invention, an outer diameter of said hollow truncated cone which is a smaller diameter is substantially smaller than an internal diameter of the blood vessel so as to guide it into the blood vessel.

Furthermore, in accordance with another preferred embodiment of the present invention, a larger diameter of said hollow truncated cone surpasses an inner diameter of the blood vessel in said at least two docking heads positioning in said vessel in about 1 to 10 mm.

Furthermore, in accordance with another preferred embodiment of the present invention, said barbs are flexible and are inclined towards a direction of said graft.

Furthermore, in accordance with another preferred embodiment of the present invention, said barbs have a length that ranges from 1 to 4 times the thickness of the blood vessel's wall.

Furthermore in accordance with another preferred embodiment of the present invention, said barbs are bent so as to establish a concave profile in respect to a radial cross section of said hollow truncated cone.

Furthermore, in accordance with another preferred embodiment of the present invention, said barbs are bent so as to establish a convex profile in respect to a radial cross section of said hollow truncated cone.

Furthermore, in accordance with another preferred embodiment of the present invention, said barbs are bent so as to establish a partial concave and partial convex profile in respect to a radial cross section of said hollow truncated cone.

Furthermore, in accordance with another preferred embodiment of the present invention, said hollow truncated cone is provided with a plurality of open slits adapted to allow said truncated cone to curtail its larger diameter.

Furthermore, in accordance with another preferred embodiment of the present invention, said truncated cone is an extension of said tubular graft that is outwardly everted over a guiding end of said at least two docking heads.

Furthermore, in accordance with another preferred embodiment of the present invention, said at least two docking heads as well as said graft are made as changeable separate modules that can be selected according to individual blood vessel anatomy to be prosthetic.

In accordance with yet another aspect of the present invention, it is further provided a delivery device adapted to facilitate the insertion of the vascular device, wherein said delivery device comprising:
  a flexible tube having a proximal side and a distal side;
  a wire passing through said flexible tube, wherein said wire extends beyond said distal side so as to enable its removal from said flexible tube;
  a sharp tip provided on said wire wherein said sharp tip is adapted to protrude through said proximal side and wherein said sharp tip can be withdrawn inwardly to within said flexible tube;
  an inflatable balloon provided in said proximal side;
  a tubing extending from said inflatable balloon to said proximal side, wherein liquid can be pushed through said tubing so as to inflate said inflatable balloon up to blood flow stoppage.

And, it is also provided in accordance with the present invention, an anastomosis method for treating a blood vessel having an aneurysm edged by healthy portions: a proximal healthy portion and a distal healthy portion, said method comprising:
  providing a graft having a length and a diameter corresponding the blood vessel to be treated, wherein said graft has a distal end and a proximal end and wherein said graft is provided with at least two docking heads that comprise a hollow truncated cone having a passage that is adapted to correspond an outer diameter of the graft and wherein said hollow truncated cone is provided with a plurality of outwardly pointing and inclined barbs, wherein a first docking heads is provided in said proximal end and at least second docking head is provided in said distal end;
  providing a delivery tool;
  stopping blood flow in the blood vessel;
  performing an incision and cleaning the aneurysm;
  inserting said proximal end to the proximal healthy portion;
  slightly pulling backwardly proximal end so as to dock said first docking head in the proximal healthy portion;
  inserting said distal end to the distal healthy portion;
  slightly pulling backwardly distal end so as to dock said at least one second docking head in the distal healthy portion;
  restoring the blood flow,
  suturing the incision.

Furthermore, in accordance with another preferred embodiment of the present invention, the method further comprising:
  providing at least one docking head that is adapted to move along said graft;
  adapting a length of said vascular device to the length of the blood vessel to be treated by moving said at least one docking head along said graft;
  fixing said at least one docking head on said graft in a suitable positioning.

Furthermore, in accordance with another preferred embodiment of the present invention, said delivery tool is a tubular catheter having a sharp tip that is adapted to be concealed, a wire adapted to be removed, and an inflatable balloon at its proximal end, wherein said method further comprising:
  puncturing the aneurysm by said sharp tip;
  concealing said sharp tip;
  advancing said tubular catheter to the proximal healthy portion;
  inflate said balloon so as to fix said tubular catheter in the proximal healthy portion and stop the blood flow;
  removing said wire;
  mounting said graft over said tubular catheter;
  guiding said proximal end to the proximal healthy portion;
  deflating said balloon and removing said tubular catheter through said graft.

Furthermore, in accordance with another preferred embodiment of the present invention, said delivery tool is forceps.

Furthermore, in accordance with another preferred embodiment of the present invention, said forceps is provided with elongated and curved jaws that can be inserted within said graft and wherein a rounded protrusion is provided at a guiding end of said elongated and curved jaws.

additionally, in accordance with another preferred embodiment of the present invention, said forceps are provided with jaws adapted to be positioned in a gap between said truncated cone and said graft so as to guide said distal end or said proximal end to the vessel healthy portion.

BRIEF DESCRIPTION OF THE FIGURES

In order to better understand the present invention and appreciate its practical applications, the following Figures are attached and references herein. Like components are denoted by like reference numerals.

It should be noted that the figures are given as examples and preferred embodiments only and in no way limit the scope of the present invention as defined in the appending Description and claims.

DETAILED DESCRIPTION OF THE INVENTION AND THE FIGURES

The present invention provides new and unique grafts for implantation in hollow organs, especially in blood vessels for treating aneurysm. The new grafts enable attaching the graft to the host vessel without the need to suture it; thus treating anastomosis in a relatively rapid manner. The suture-less anastomosis is performed in the distal side as well as in the proximal side of the aneurysm so as to accomplish the anastomosis with minimal loss of blood.

According to the anastomosis method provided herein, the graft is prepared to a required size, blood flow is stopped for relatively short while in the sick vessel, aneurysm incision and clearing is performed and the graft is introduced and installed in the aneurysm. The non-suture ends connection of the graft to the vessel provides leak proof sealing of the connections and rapid blood supply restoration.

The graft is being prepared to fit the required size according to the patient's vessel dimensions. This is performed prior to the operation. In some of the embodiments disclosed here, modular parts are provided so as to facilitate the leak-proof connection between the graft and the vessel.

In a preferred aspect of the present invention a vascular device is provided for treating a blood vessel with aneurysm. The vascular device comprises a graft, which can be a tubular or bifurcated graft, having a proximal portion and a distal portion. A first docking head is provided at the proximal portion and a second docking head is provided at the distal portion. If the graft is a bifurcated one, both ends of the distal portion are provided with the docking heads. The vascular device is coupled to the blood vessel on both sides of the aneurysm so as to replace this portion of the blood vessel by the first docking head and the second docking head. The docking heads act as guiding, anchoring and sealing means in a suture-less and rapid manner.

In another preferred aspect of the present invention, the graft that is prepared prior to the opening of the aneurysm area is longer than the sick vessel portion itself and the docking head that is provided at an end of the graft is mounted so as to allow movement of the docking head along the end portion of the graft. During the anastomosis, the surgeon can adjust the docking head or at least one of the docking heads and fasten it or them at the ends of the graft in the required place according to the situation that is revealed after actual opening of the aneurysm. The docking head can be fastened by any of the conventional means such as a fit, glue, suture, clips, staples. Any other technique for attaching the docking head in the required place on the graft is covered by the scope of the present invention.

Figure 1:
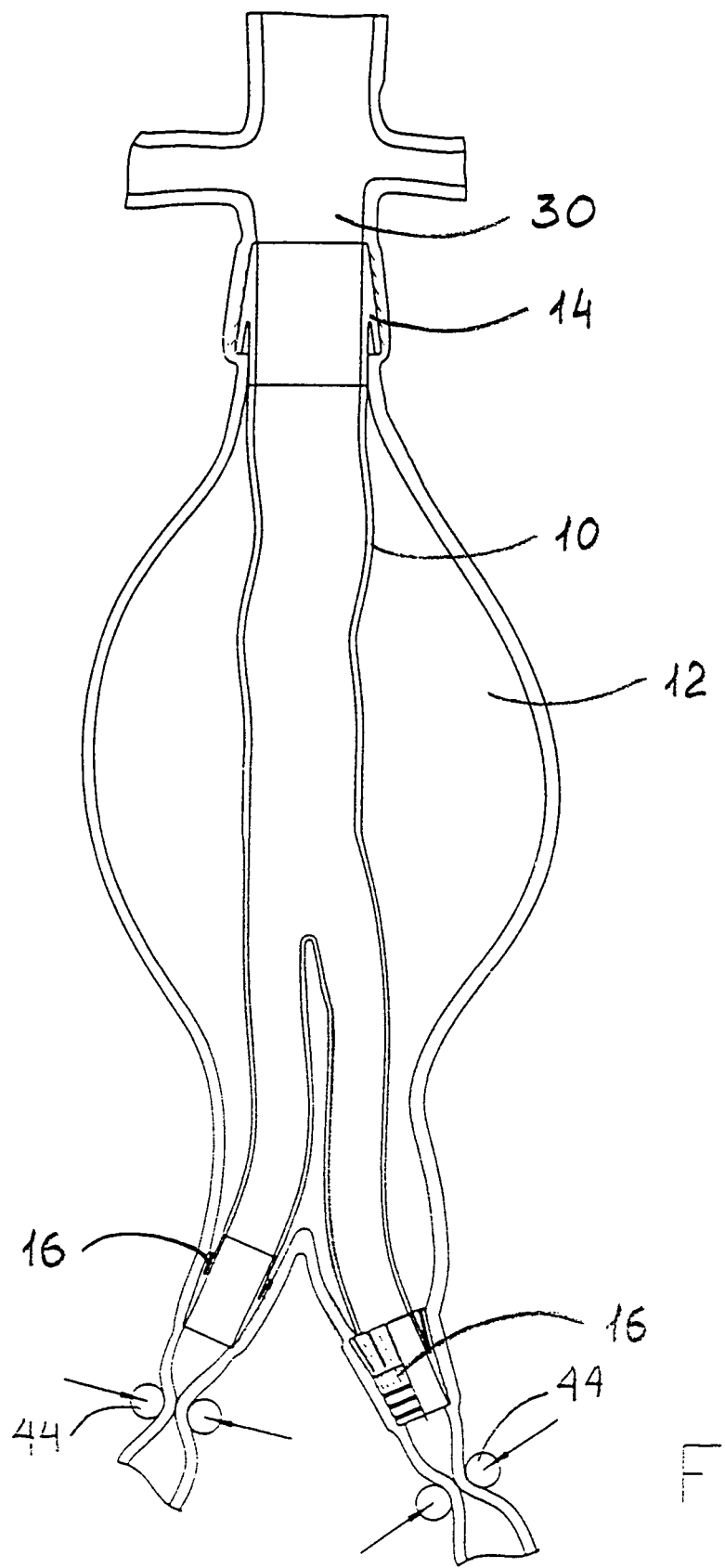
FIG. 1 illustrates a cross sectional view of a bifurcated graft in accordance with a preferred embodiment of the present invention, inserted within an aortic aneurysm.

Reference is now made to FIG. 1 illustrating a cross sectional view of a bifurcated graft in accordance with a preferred embodiment of the present invention, inserted within an aortic aneurysm. A bifurcated graft 10 is inserted within an aneurysm 12 in a blood vessel. Three ends of bifurcated graft 10 are provided with concentric docking heads, a first docking head 14 at the proximal end and two docking heads 16 at the distal ends of the graft. Docking heads 14 and 16 are adapted to couple the graft to the vessel without suturing it and provides the surgeon with the ability to rapidly connect the graft to the aneurysm. The docking head according to the present invention has three functions: guiding the graft into the vessel, anchoring it into the inner wall of the vessel and sealing it so as to provide a continuous wall that prevents blood from leaking out of the vessel. The procedure of inserting the graft in the aneurysm is explained herein after.

Figure 2:
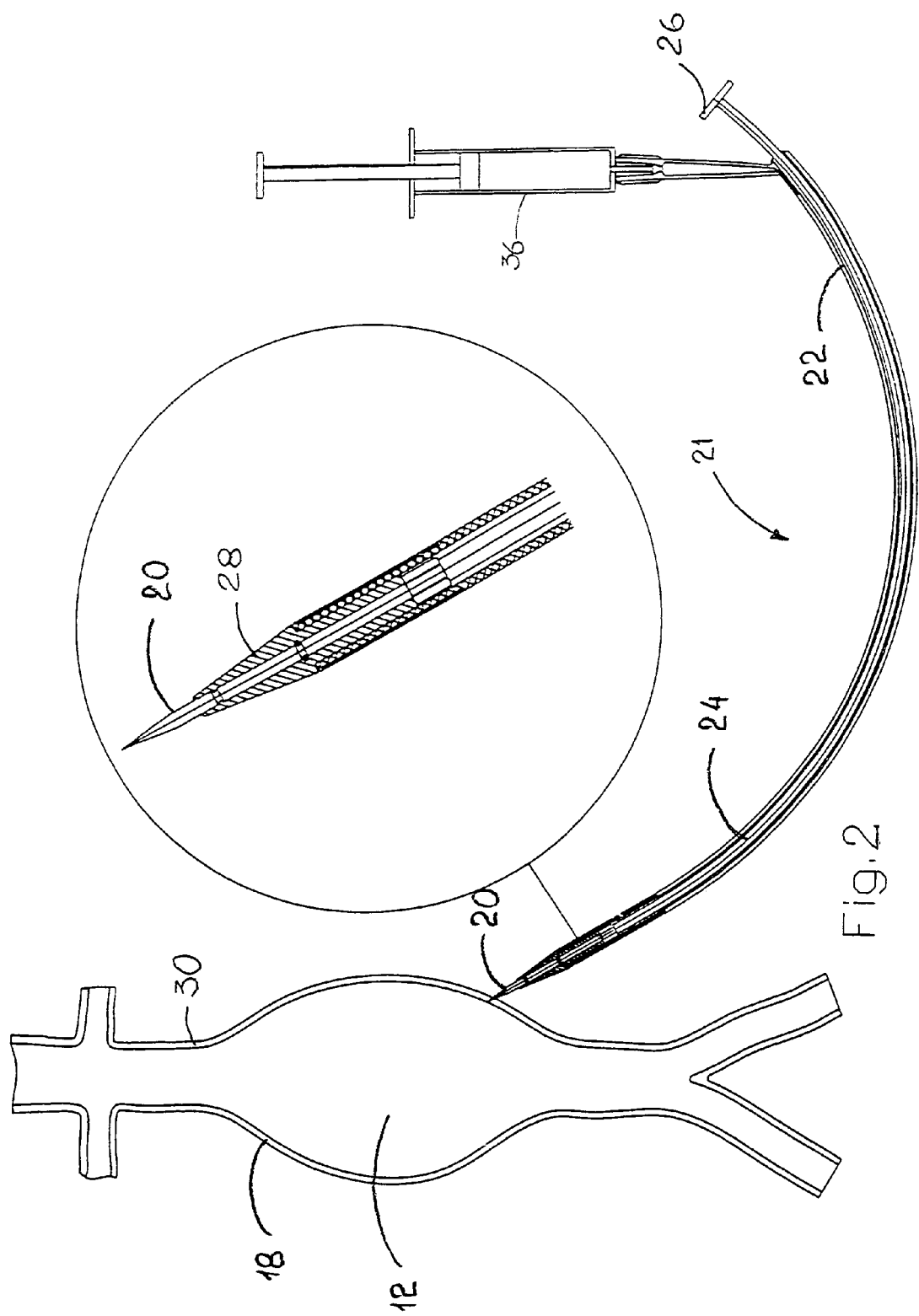
FIGS. 2-3 illustrate the procedure of opening an access to the aneurysm by a catheter in accordance with a preferred embodiment of the present invention.
Figure 3:
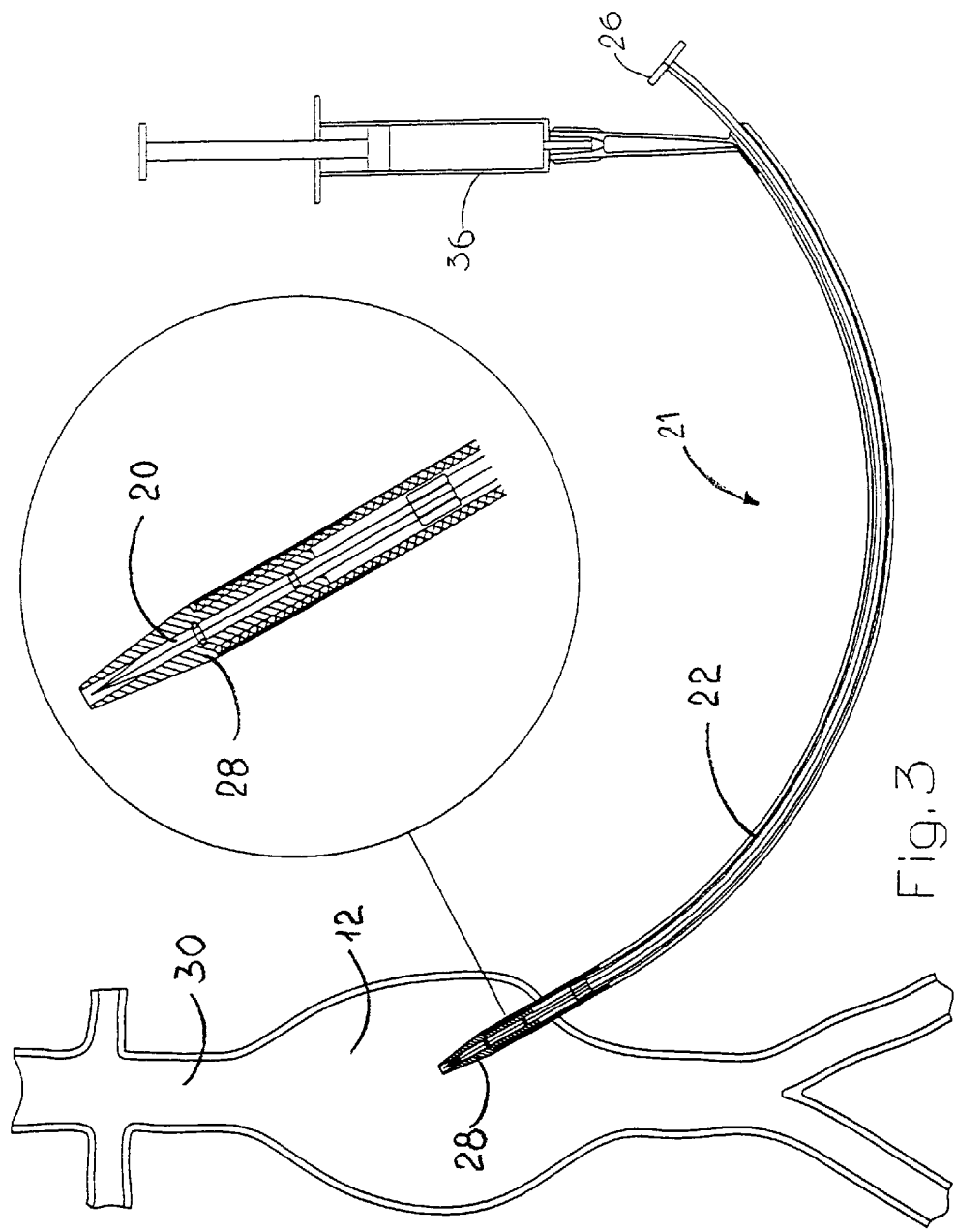
Figure 4:
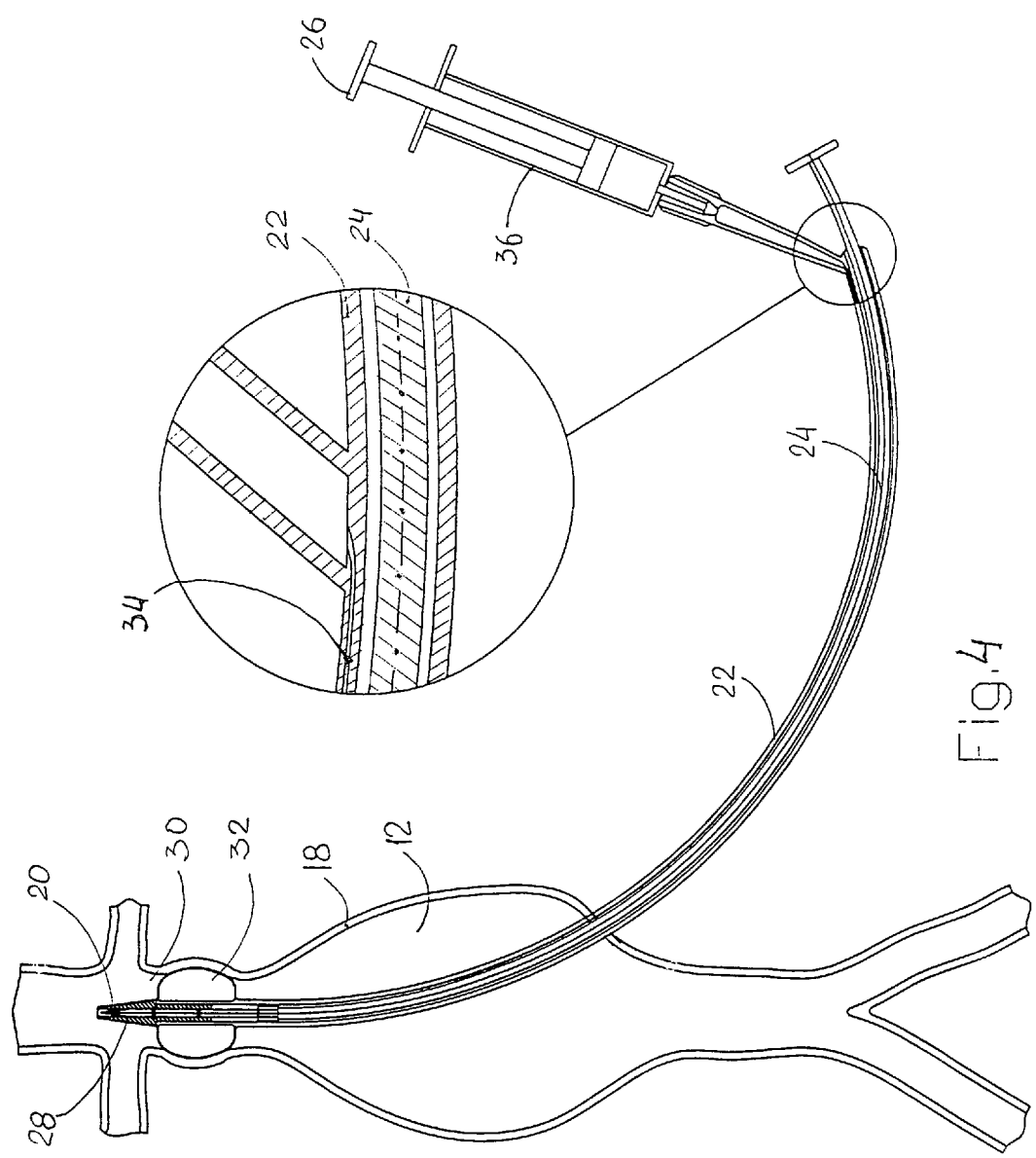
FIG. 4 illustrates the delivery catheter fixed on top of the aneurysm, ready for insertion of the proximal side of a graft in accordance with a preferred embodiment of the present invention.

Reference is now made to FIGS. 2-4 illustrating the procedure of opening an access to the aneurysm by a delivery catheter in accordance with a preferred embodiment of the present invention. FIG. 2 illustrates a delivery catheter 21 that is basically a catheter tube 22 provided with a sharp tip 20 (sharp tip 20 is shown in an enlarged view and act as a stylet) that is used to puncture a wall 18 of aneurysm 12 and enter within the vessel. Sharp tip 20 is connected to a wire 24 that passes through catheter tube 22 and facilitates in its insertion. Sharp tip 20 is provided with a withdrawal means 26 at its distal end. As shown in FIG. 3, after the proximal side of catheter tube 22 is within aneurysm 12, sharp tip 20 is slightly withdrawn into the catheter's body. Sleeve 28 (can be seen clearly in the enlargements in FIGS. 2 and 3) receives sharp tip 20 so that no additional puncturing is performed once the catheter's proximal side is within the vessel. Catheter tube 22 is pushed further into the vessel so that its proximal side resides within the healthy neck portion of the vessel 30. As shown in FIG. 4, after positioning the proximal side of delivery catheter 21 within neck 30, a laterally inflatable balloon 32 that is provided in the proximal portion of the catheter is inflated so as to establish a firm hold of catheter tube 22 in neck 30. The surface of inflated balloon 32 is covered with an antifrictional structure which is not cooperating with blood. Delivery catheter 21 is provided with a special tube 34 that extends from its distal side (shown in the enlargement in the Figure) to the balloon in its proximal side wherein liquid can be inserted by a syringe 36 into tube 34 so as to inflate balloon 32. Catheter tube 22 provided with wire 24 is used to guide the graft into the right positioning in the aneurysm's proximal neck. After the catheter is firmly installed within the neck of the vessel and in accordance with a preferred embodiment of the present invention, the graft can be guided onto the delivery catheter and into the aneurysm.

Figure 21:
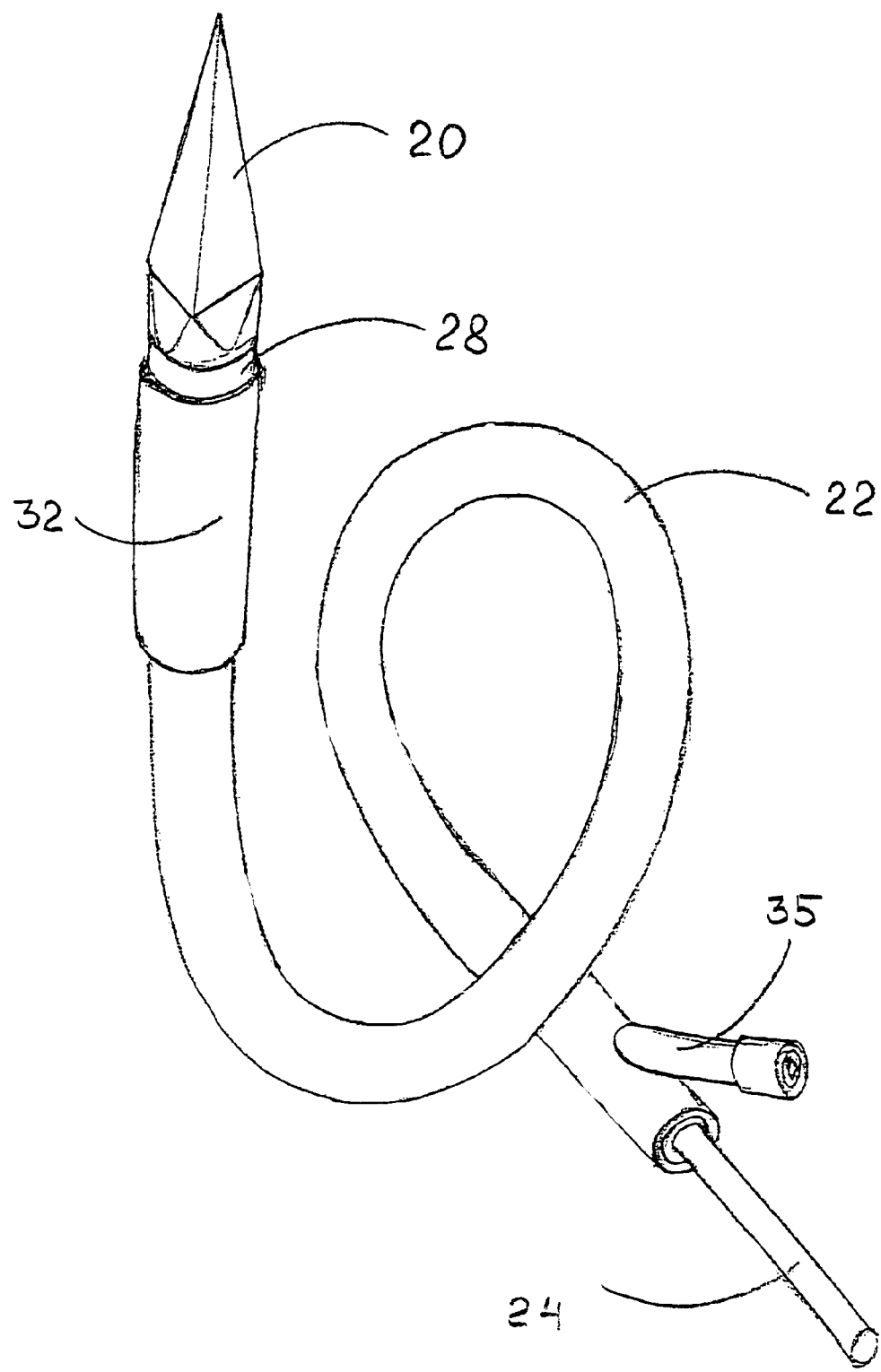
FIG. 21 illustrates a perspective view of a delivery catheter for facilitating the insertion of a graft in accordance with a preferred embodiment of the present invention.

Reference is now made to FIG. 21 illustrating a perspective view of a delivery catheter for facilitating the insertion of a graft in accordance with a preferred embodiment of the present invention. Catheter tube 22 is provided with sharp tip 20 that is adapted to puncture the aneurysm as shown herein before so as to enter into the vessel. Sharp tip 20 is connected to the proximal end of the catheter through a wire 24 that partially protrudes from the proximal side of the catheter and its end act also as withdrawal means 26 to withdraw sharp tip 20 to within sleeve 28. Wire 24 is adapted to maintain catheter tube 22 stiff when it is inserted countercurrent to the blood flow and into the proximal neck of the vessel. After the balloon is inflated in the neck as explained herein before, wire 24 can be fully removed through the catheter's distal end using withdrawal means 26. The delivery catheter is provided with a side extension 35 adapted to deliver liquid from a syringe (not shown in FIG. 21, shown in FIGS. 2-5) that is connected to the extension through a tubing so as to inflate a balloon (shown in FIG. 21 in an un-inflated position). When wire 24 is withdrawn from catheter tube 22, the catheter is fully flexible.

It should be noted that the delivery catheter as disclosed in the present invention is adapted to stop the blood flow through the aneurysm's proximal neck when the installation of the graft is performed. In prior art procedures, the length of the neck is crucial in determining whether to do the procedure or not, and a relatively short neck between the aneurysm and the renal arteries will result in avoiding the procedure all together since there is no possibility to perform such a long procedure while preventing blood from flowing into the renal arteries. In the procedure disclosed herein, the proximal portion of the delivery catheter is pushed into the neck and the balloon that is provided in the proximal portion can be inflated also in a relatively short neck. Moreover, the balloon can be also inflated in the area of the renal arteries connection or even above them so that the blood to the kidneys is stopped. Since the procedure of graft implantation in accordance with the present invention is rapid, the blood flow to the kidneys can be stopped for that short while. Therefore, even an aneurysm having a relatively short proximal neck can be treated (FIG. 5 illustrates a case in which the blood flow to the renal arteries is being blocked).

Figure 5:
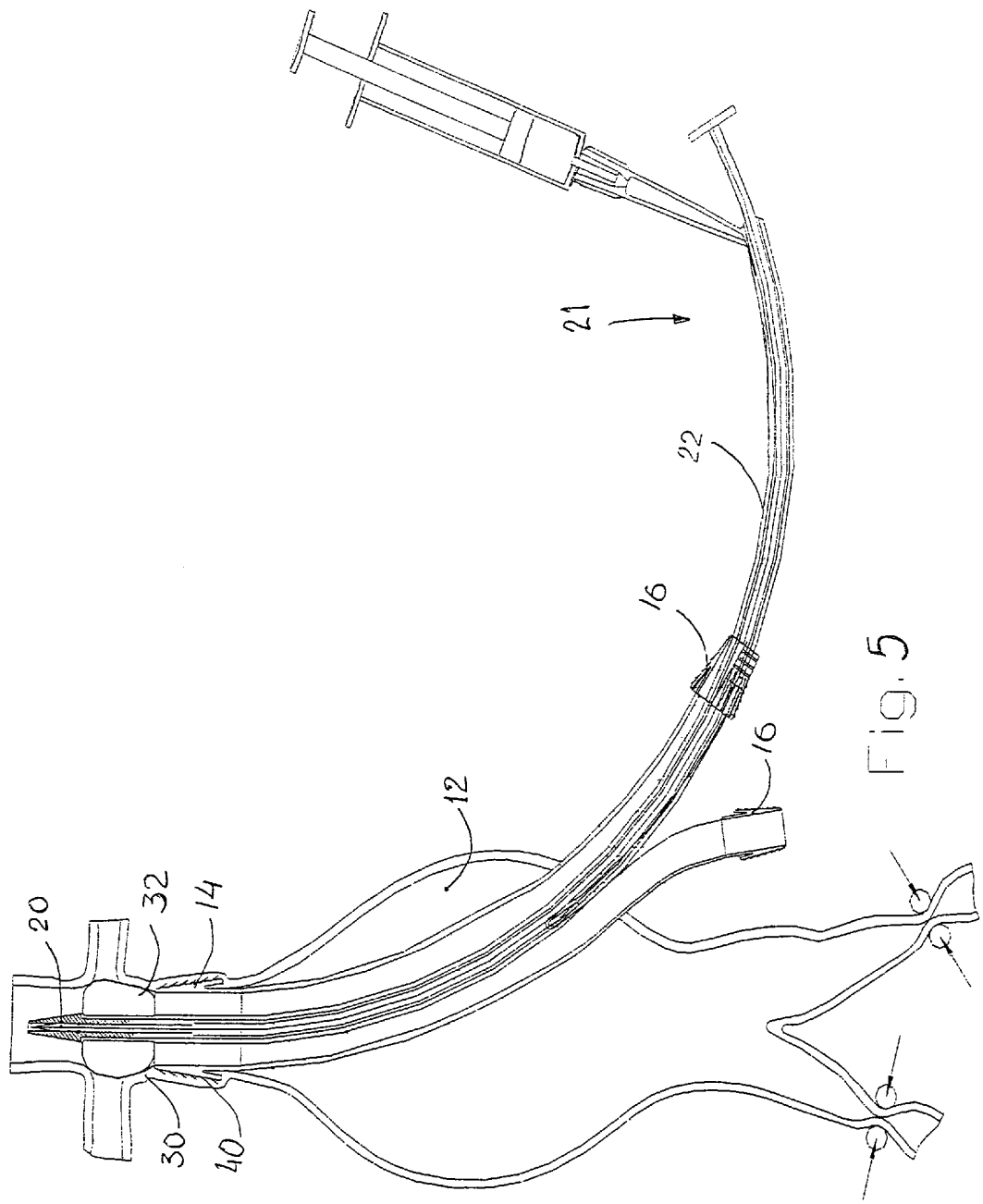
FIG. 5 illustrates a cross sectional view of the bifurcated graft shown in FIG. 1, inserted in a proximal neck of the aneurysm in the vessel along the catheter shown in FIGS. 2-4.
Figure 6:
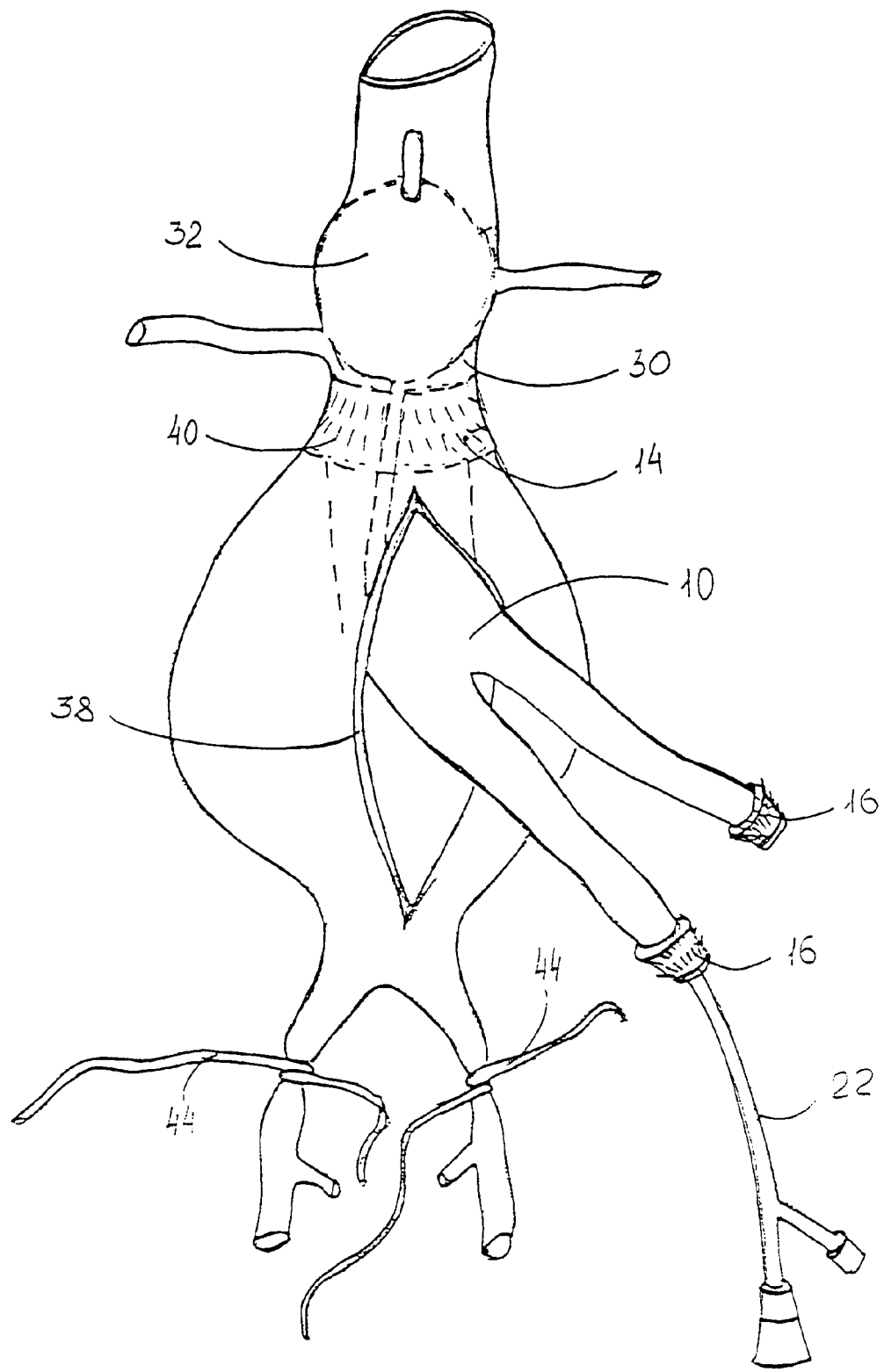
FIG. 6 illustrates a perspective view of the bifurcated graft shown in FIG. 1, passing over catheter tube up to its proximal end.

Reference is now made to FIGS. 5 and 6 illustrating a cross sectional view and a perspective view of the bifurcated graft shown in FIG. 1, inserted in a proximal end of an aneurysm in the vessel along with a catheter. Since balloon 32 stops the blood from flowing towards aneurysm 12, the vessel can be now cut without loose of blood and in order to guide the graft onto catheter tube 22. Bifurcated graft 10 is guided over catheter tube 22 while the proximal side of the graft 10 is inserted into healthy vessel neck 30 for docking. As mentioned herein before, docking the graft into the neck of the vessel using a docking head eliminates the need to suture the graft to the vessel as performed in prior art procedures. The docking procedure is relatively rapid.

In order to firmly and sealingly couple the graft to the vessel, docking head 14 is inserted into neck 30. The types of docking head will be comprehensively explained herein after, however, basically, docking heads 14 and 16 are conical structures provided with a plurality of inclined barbs 40. Inclined barbs 40 are arranged at the circumference of the conical structure in at least one row and are distally pointed to the direction of the graft's body. The conical structure followed by the graft is inserted into neck 30 through its narrow end while inclined barbs 40 smoothly pass through a portion of the neck. Then, docking head 14 is being slightly pulled back. Upon pulling back the conical structure, inclined barbs 40 are being imbedded within the neck, forming a firm and sealed connection between the vessel and the graft. The mechanism used in order to anchor the graft in the vessel's inner wall is similar to the mechanism of a bee's sting. Pulling docking head 14 backwardly replaces the time consuming suturing procedure that takes place in the prior art grafting.

Figure 19:
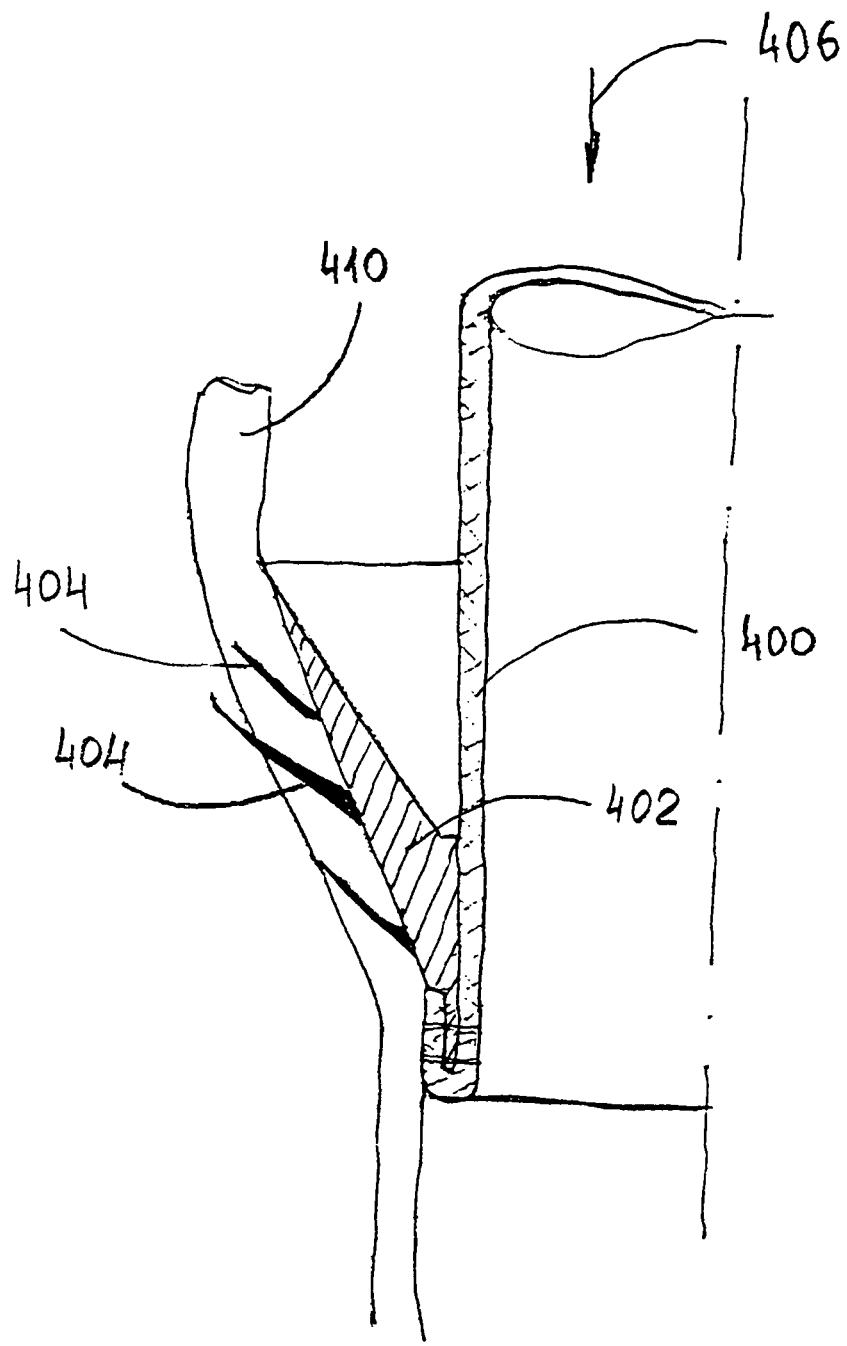
FIG. 19 illustrates an enlarged view of a docking head in accordance with a preferred embodiment of the present invention, nailed to the vessel.
Figure 20:
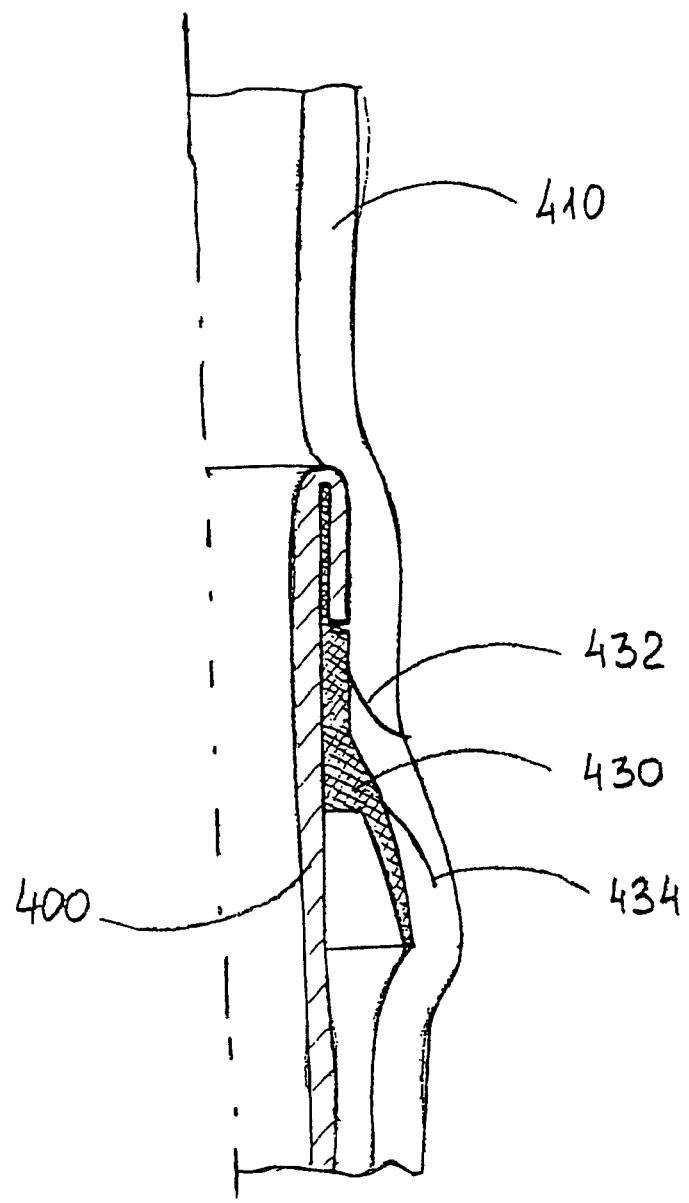
FIG. 20 illustrates an enlarged view of a docking head in accordance with another preferred embodiment of the present invention.

Reference is now made to FIG. 19 and FIG. 20 illustrating an enlarged view of docking heads in accordance with preferred embodiments of the present invention, nailed to the vessel's inner wall. In FIG. 19, graft 400 is provided with a docking head 402, adapted to connect the graft to the circumference of a vessel 410. Barbs 404 are pointed backward; opposite the direction to which graft 400 is pushed (this direction is marked by arrow 406). The barbs can be concaved relative to the profile of the graft, convex or partially convex and partially, concaved so that they can be nailed into the blood vessel wall. Those shapes of the barbs prevent them from contiguously bend on the graft's wall without sticking into the blood vessel's wall. After positioning of the graft, graft 400 is pulled slightly backwardly so as to nail barbs 404 into vessel 410. In FIG. 20, graft 400 is provided with docking head 430 that has a concaved profile that facilitates its insertion into vessel 410. Docking head 430 is provided with barbs that are connected to the docking head in different positions. Barb 432 is connected in a concaved orientation while barb 434 is connected in a convex orientation. Different types of barbs orientations provide a firm coupling between vessel 410 and docking means 430 so as to sealingly block any blood leakage from the vessel. The orientations of the barbs also provide firm anchoring of the graft within the vessel so that there will be substantially no relative movement between the two.

Figure 7:
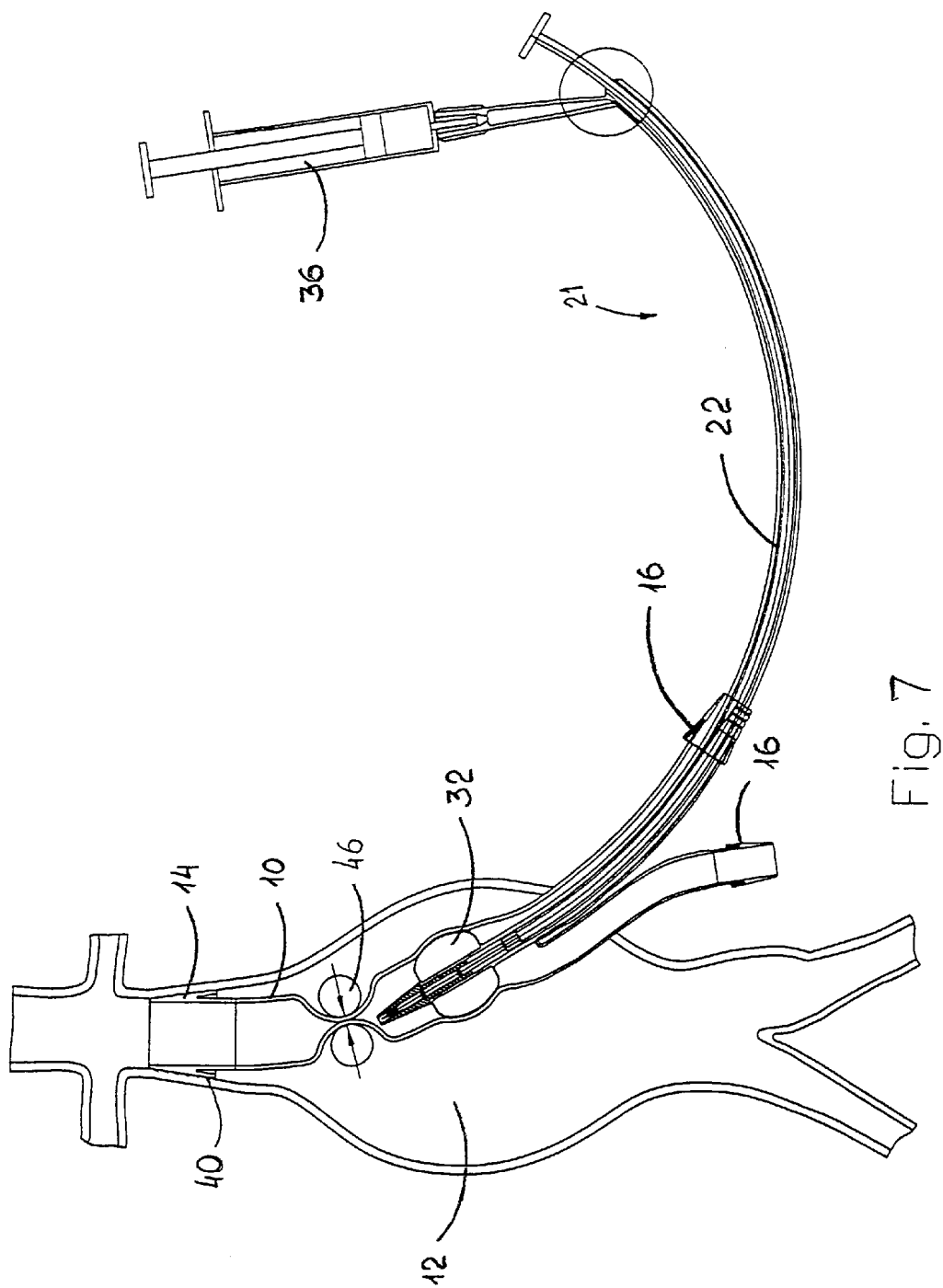
FIG. 7 illustrates a cross sectional view of the graft shown in FIG. 1 in an advanced stage of catheter removal in accordance with a preferred embodiment of the present invention.

Reference is now made to FIG. 7 illustrating a cross sectional view of the graft shown in FIG. 1 in an advanced stage of graft insertion in accordance with a preferred embodiment of the present invention. At this point, delivery catheter 21 is being removed. Balloon 32 is being slightly deflated so as to the accord the graft diameter and is being withdrawn towards the proximal portion of the graft. The removal of delivery catheter 21 allows blood to flow into the graft. In order to prevent blood loose, clip 46 is clamped on graft 10 in an area from which delivery catheter 21 had been already removed. At this point, delivery catheter 21 is being completely withdrawn from within the graft. The fact that a proximal clip is removed in this stage to the graft itself is very significant especially in cases in which the proximal healthy neck is relatively short and the renal arteries are being blocked. As mentioned herein before, in cases the healthy neck is relatively short and there is a need to block the renal arteries for the procedure, the whole procedure is being relinquished since the damage to the kidneys may be beyond repair. Due to the devices and the methods of the present invention, the blockage of blood to the kidneys is for a very short time and there is almost no risk involved in the procedure. The blood flow to the kidneys is restored before the distal docking is performed.

Reference is being made again to FIG. 1 illustrating a cross sectional view of the bifurcated graft in accordance with a preferred embodiment of the present invention, inserted within an aortic aneurysm. Bifurcated graft 10 is connected in the proximal side to the vessel's neck 30 and is now ready to be connected in its distal side to the two vessels that bifurcate from aneurysm 12. As mentioned herein before, graft 10 bifurcates into two portions in its distal side. Both portions are being connected to both vessels in the same way as the connection of the graft to the proximal neck. For that, each bifurcation is provided with docking head 16 that is basically similar to docking head 14 and is also provided with elastic barbs that are directed towards the graft itself. The connection is immediate and simple while graft 10 is positioned so as to allow docking head to be placed in the healthy distal vessels. Docking heads 16 are pushed into the vessels and than slightly pulled outwardly so that the elastic barbs are nailed into the vessel and sealingly and firmly connect bifurcated graft 10 to the vessels. Just before the actual connection of the distal sides to the vessel, clip 46 (not shown in FIG. 1) is removed so as to establish a flow of blood through the graft. After the connection is complete, clips 44 can be removed so as to establish a blood flow to the blocked areas.

It is important to emphasis again that since the new procedure is a rapid one due to the use of docking heads instead of suturing, the blockage of blood to the areas that receive blood through the treated vessel is for relatively short while. One of the features that may have lethal consequences of any procedure in which aneurysm is treated is the blockage of blood flow through this vessel during the whole operation. One of the major faults of the prior art procedures is the fact that the connection of the graft to the vessel is extremely time consuming, even for a very experienced surgeon. Using the procedures and grafts provided in the present invention markedly reduces the time of operation so that the blood is blocked just to a minimum time necessary to dock the graft in the vessel.

Figure 8:
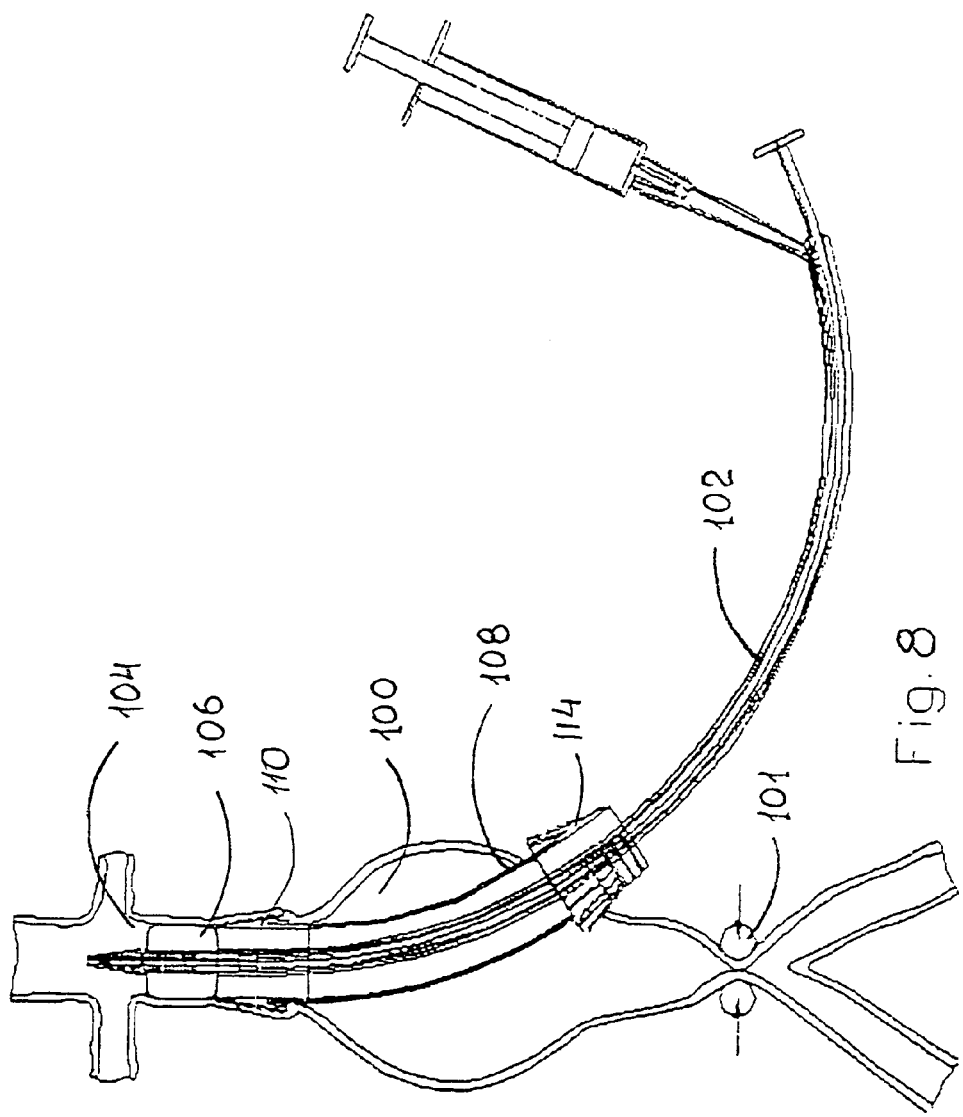
FIGS. 8-13 illustrate stages of a tube graft installation in a vessel with aneurysm in accordance with other preferred embodiments of the present invention.
Figure 9:
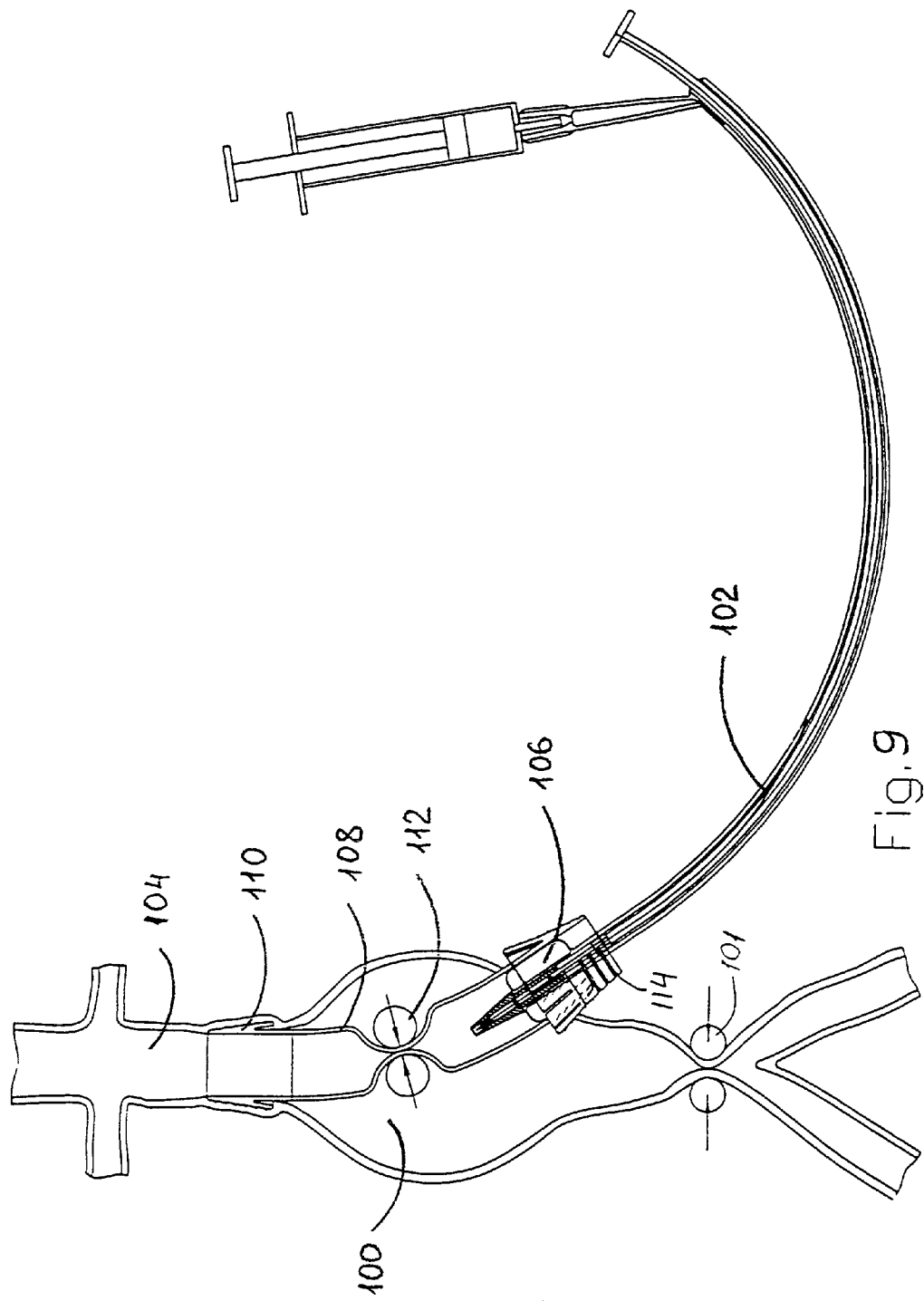
Figure 10:
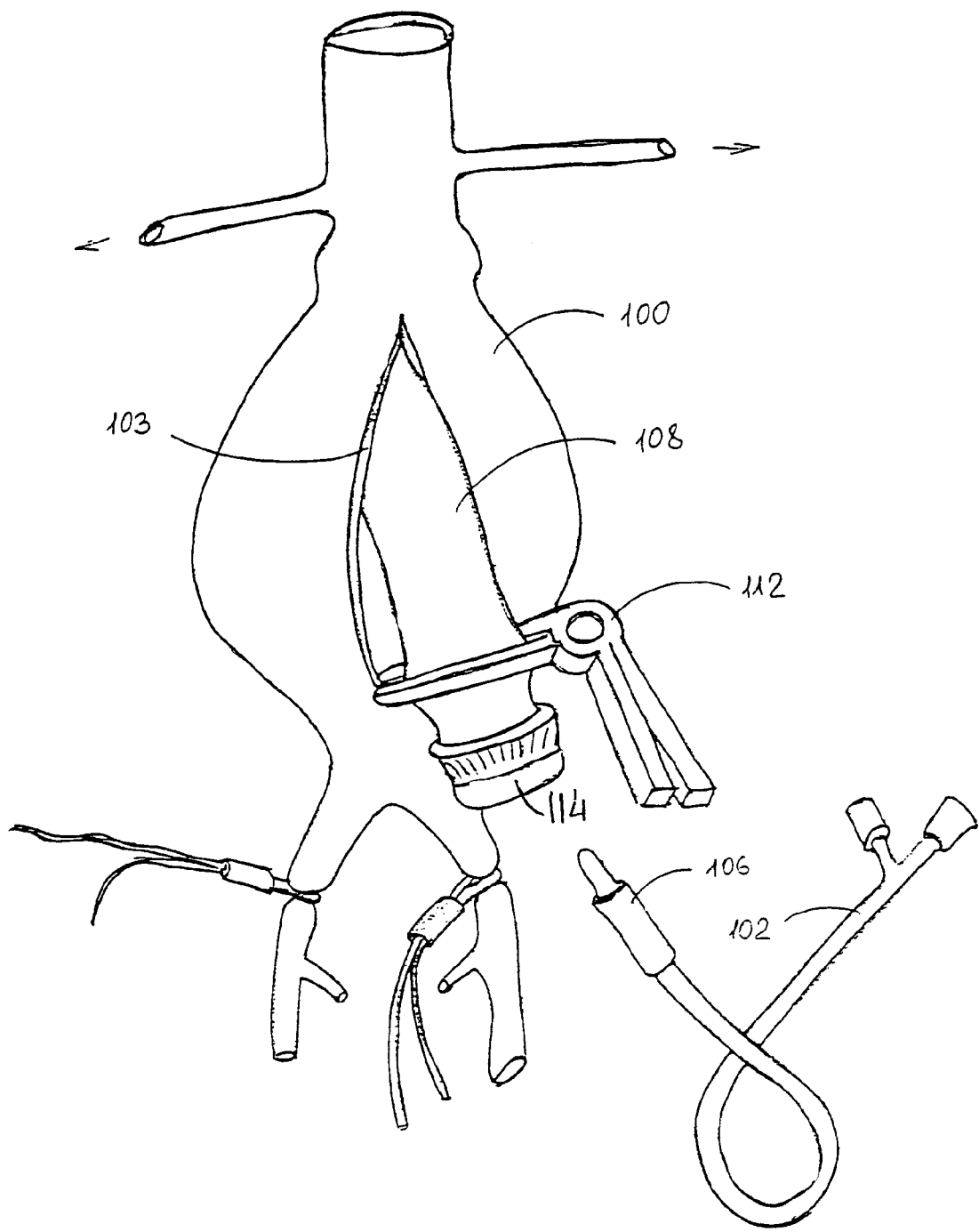
Figure 11:
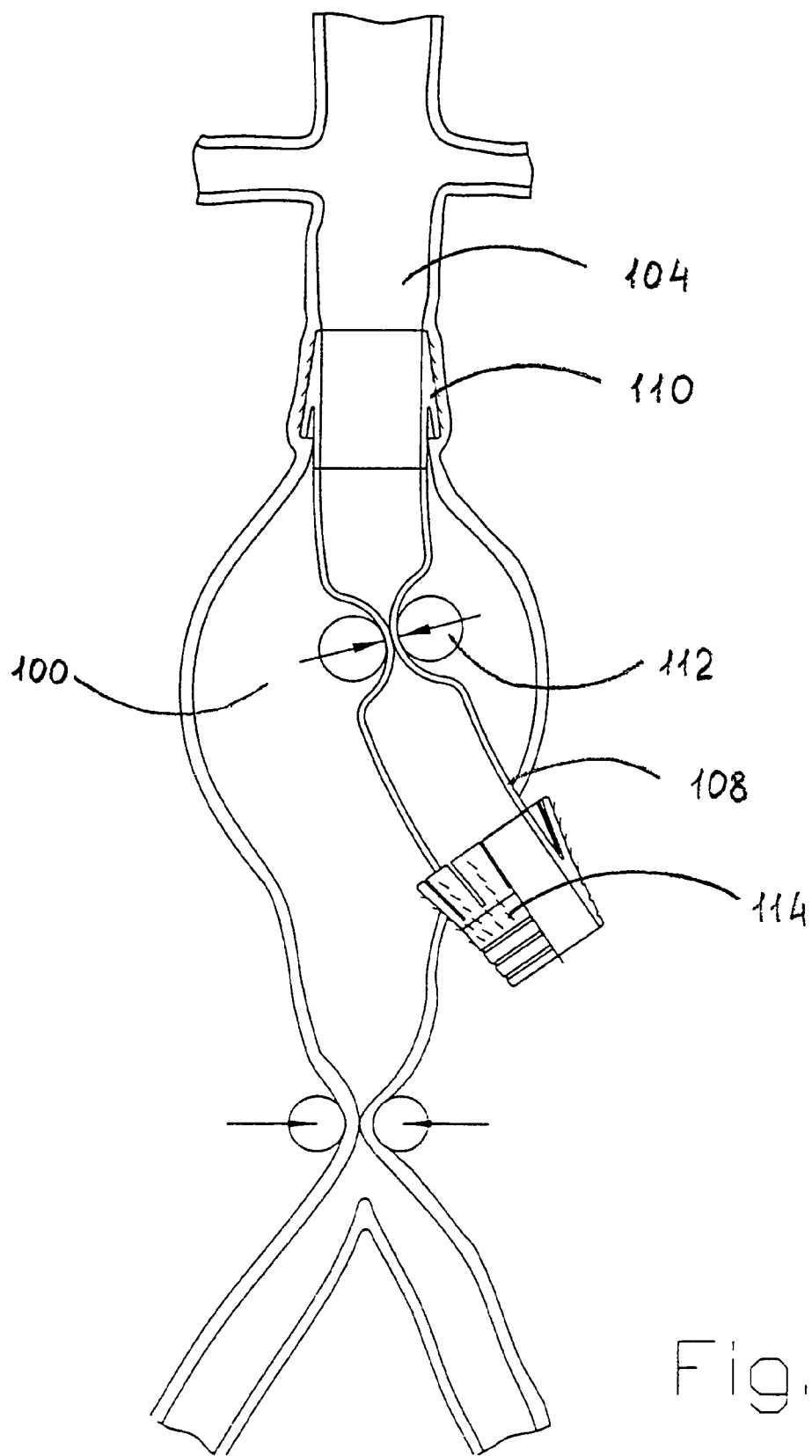
Figure 12:
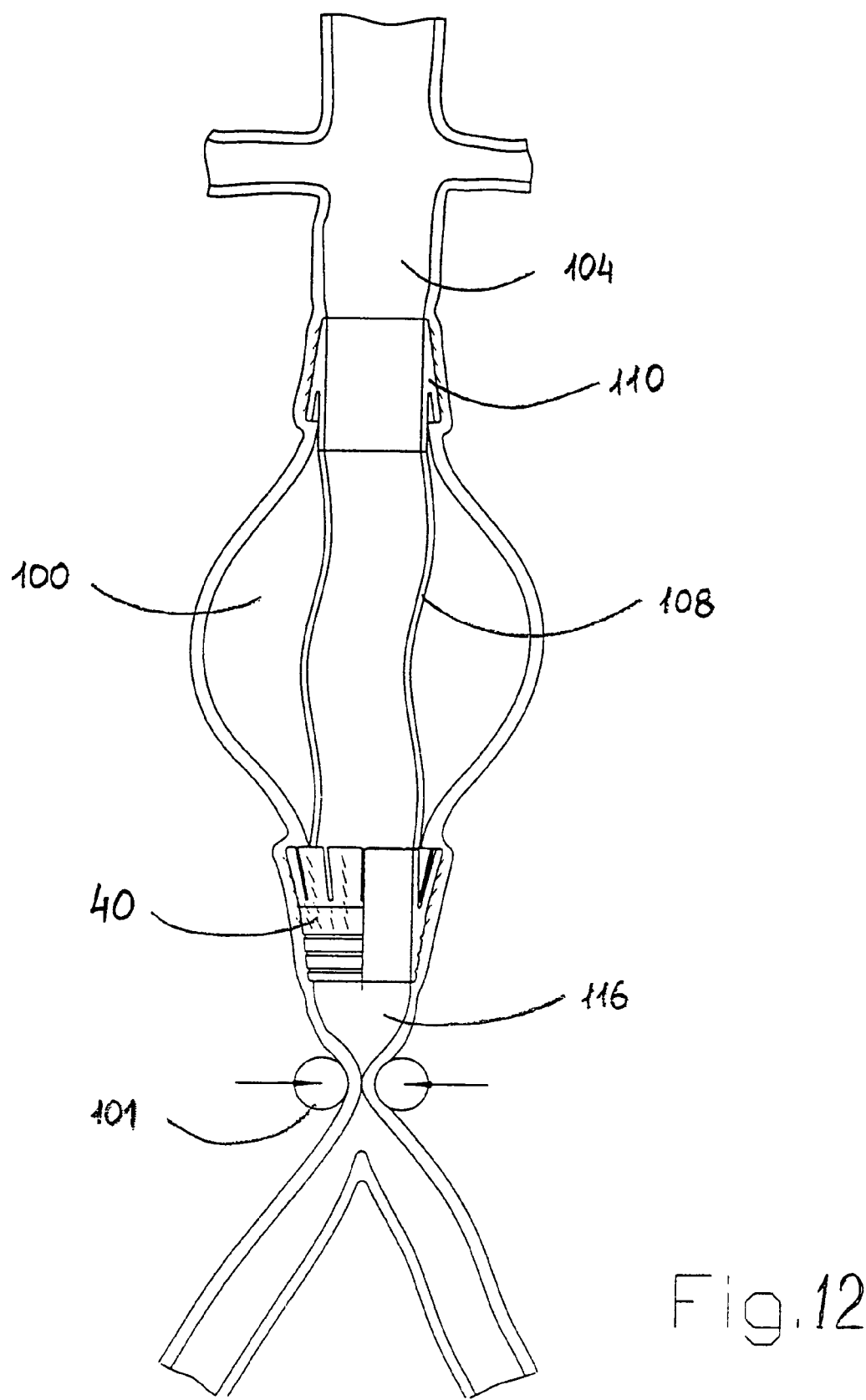

Reference is now made to FIGS. 8-13 illustrating stages of graft installation in a vessel with aneurysm using a delivery catheter in accordance with another preferred embodiment of the present invention. In cases the aneurysm is in the upper portion of the aorta, for example, and there is still a healthy portion before the bifurcation of the vessel, one can use a straight graft such as the graft shown herein. According to angiographic results, the graft approximate measures can be taken and a suitable graft can be prepared. Than, midline laporotomy is performed so as to approach the infrarenal abdominal aorta and exposing the aneurysm's necks. Vascular clamps are being positioned. FIG. 8 illustrates an aorta having an aneurysm 100 in the upper portion. The procedure is similar to the procedure described already herein, puncturing the side wall of aneurysm 100 by a catheter 102, positioning it in the vessel's healthy neck 104 and inflating a balloon 106 so as to firmly maintain catheter 102 for graft guidance. While the aneurysm is being punctured by the delivery device, the blood in the proximal neck can be stopped even with a finger due to the very short act. Vascular clamping is performed in the distal side of aneurysm 100 by vascular clamp 101 and in the proximal portion, by balloon 106. The size of the graft is being evaluated again and fixed to suit the size of aneurysm. Then, an incision in the side wall of the aneurysm is performed as well as suctioning the blood residuals so as to allow a graft 108 to be mounted onto delivery catheter 102 (incision 103 is shown in FIG. 10). Similarly to bifurcated graft 10, graft 108 is provided with docking heads. A first docking head 110 is provided in the distal end of graft 108 that is being guided onto catheter 102. Docking head 110 is advanced into neck 104 and then pulled back so as to nail the flexible barbs into the wall of the proximal neck.

Figure 13:
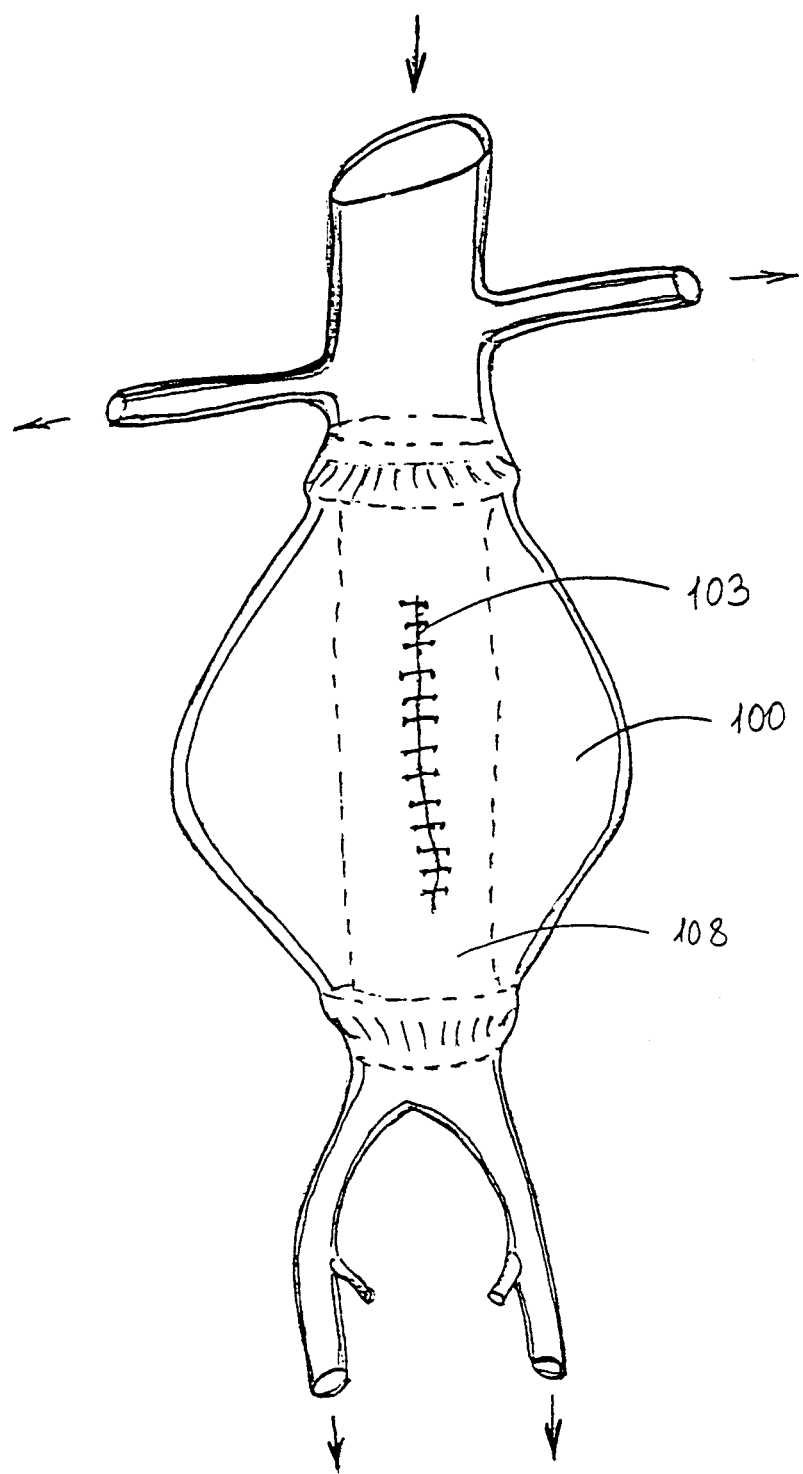

After the proximal end of graft 108 is firmly secured within neck 104, balloon 106 is slightly deflated so as to allow its withdrawal through graft 108 as shown in FIGS. 9 and 10. Catheter 102 is withdrawn and a clip 112 is clipped onto graft 102 so as to stop blood flow. The distal portion of graft 108 is free to be docked into the distal neck of the vessel. Docking head 114 is inserted into the aneurysm and positioned within the distal healthy neck 116. Again, due to the elastic barbs provided on docking head 114, its connection to the neck is very quick and firm by advancing the docking head forward and then slightly withdrawing it backwardly so that the barbs are nailed into the neck. Vascular clamp 101 can be removed so as to restore blood flow to the portions of the body that receives blood from the vessel. FIG. 13 shows the vessel after incision 103 is sutured. This procedure can be performed also using another delivery device other then a delivery catheter as will be shown herein after.

Figure 14:
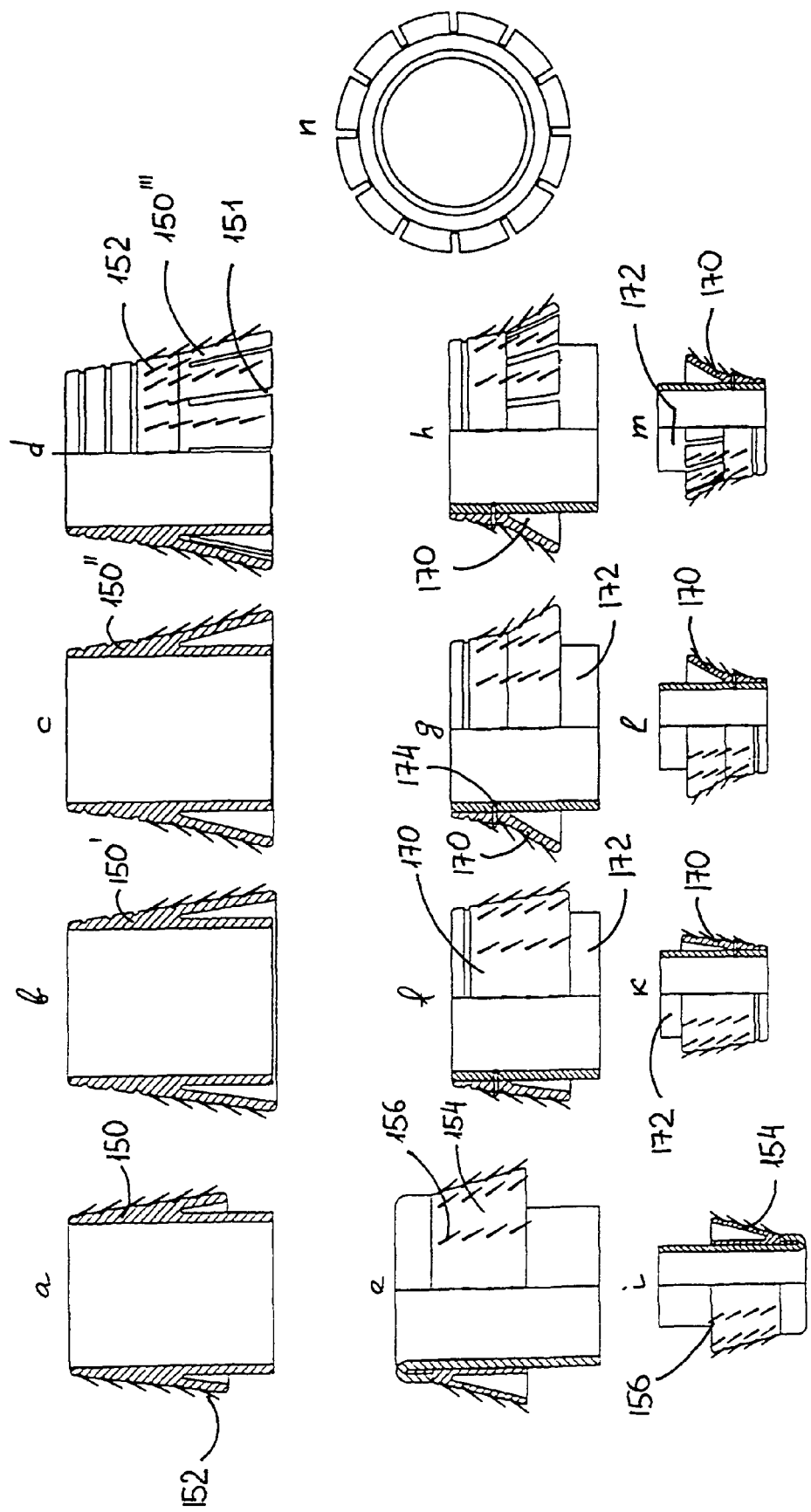
FIGS. 14a-n illustrate views of various configurations of docking heads in accordance with several preferred embodiments of the present invention.

Reference is now made to FIGS. 14*a-n* illustrating views of various configurations of docking heads in accordance with several preferred embodiments of the present invention. The docking heads shown herein are adapted to connect the graft within the vessel in a suture-less manner so as to establish a firm and secured connection as well as a connection that fully seals the vessel so as to ensure that there is no leak of blood through the connections. Generally, the docking heads are hollow thin-walled elastic truncated cones that are mounted onto the end of the graft. The small diameter end of the cone is fitted to the external diameter of the vessel and the bigger diameter surpasses it for about 1-10 mm. The cones can be concaved as shown in embodiments g, h, l, and m so as to facilitate its insertion into the aneurysm's neck; however, they can be straight as in a-f or convex. The cones are provided preferably with elastic barbs on the cones external surface. The barbs are inclined relative to the cone and are directed to the direction of the graft's body. It is preferable that the length of the barbs will not exceed the thickness of a wall of the vessel so as to prevent puncturing the vessel.

In FIGS. 14*a-d*, the docking head is a conical structure 150, 150', 150" and 150'" respectively. The conical structure can be of relatively short length (150) or longer (150"), depending on the length of the healthy portion of the neck in which it has to be coupled. The conical structure is provided with a plurality of barbs 152 that are adapted to nail into the neck at the edges of the aneurysm. Barbs 152 are preferably flexible. It is shown in embodiment d that the cone is provided with slits 151 that enables the cone to curtail from its outer diameter when it is introduced into the neck so as to facilitate its insertion. The slits can be of about 0.3-0.6 cm.

FIG. 14*e* and illustrate conical structures 154 that are produced by outwardly everting the end of the graft's body so that the truncated cone is an extension of the graft. The truncated cone is provided with bards 156.

Modular docking heads are shown in FIGS. 14*f-h* and 14*k-n*. The modularity of the docking head provides the device with versatility so that the surgeon can decide in any stage of the operation which docking head to use. A truncated cone 170 is mounted on the edge of graft 172 and is connected to it by a connector 174. The advantage in these types of docking heads is that the type can be chosen of a plurality of different types even during operation when the surgeon can adapt the right cone that suits the inner structure of the particular vessel. The length of the cone as well as its angle can be different. The surgeon can prepare in advance an elongated graft having a stable docking head in the graft's proximal end and a modular docking head that is slidably provided in the distal portion of the graft. After the surgeon docks the proximal docking head of the graft in the proximal neck, he may measure in real time the actual length of the graft and stabilize the slidable distal docking head in a suitable place while the residual graft can be cut. In any of the embodiments, plurality of barbs is provided on each one of the cones.

Figure 15:
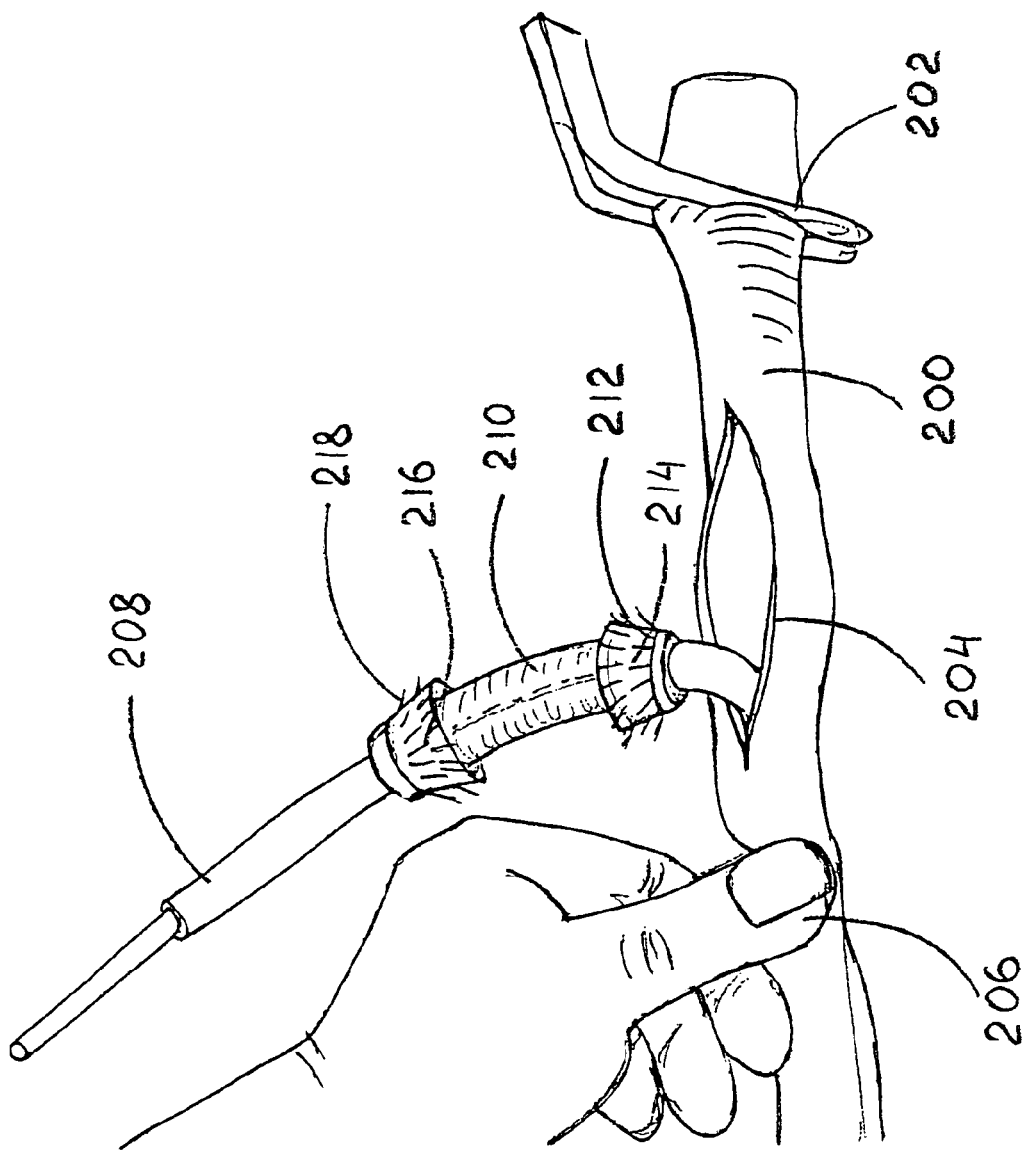
FIG. 15 illustrates an isometric view of graft insertion into aorta guided by a delivery catheter tube in accordance with another preferred embodiment of the present invention.

Reference is now made to FIG. 15 illustrating an isometric view of graft insertion into aorta guided by a delivery device in accordance with another preferred embodiment of the present invention. Since the procedure in accordance with the present invention is very quick and there is a desired to stop the blood flow to the organs for a minimum amount of time, the proximal portion of a vessel 200 can be clipped with a vascular clamp 202 so as to stop the blood flow to the aneurysm area. An incision 204 is performed in the aneurysm area while a finger 206 blocks the proximal side of the vessel. Alternatively, another vascular clamp can be used in order to block the proximal side. A guide 208 is inserted into the proximal portion of vessel 200 while a graft 210 is mounted on guide 208. After the positioning of the guide in the healthy neck in the proximal side of the vessel, the proximal side of graft 210 is placed within the corresponding neck while pulled slightly outwardly in order to nail barbs 212 of docking head 214 in the distal neck. Guide 208 is then removed and the proximal portion of graft 210 is inserted within the vessel. Docking head 216 that is connected to the distal side of graft 210 is placed within the distal portion of the healthy vessel's neck while pulled slightly outwardly in order to nail bards 218. The blood flow then can be restored.

Eliminating the need to suture the graft to the proximal and distal portions of the vessel enables a rapid procedure, and offers the use of many other delivery devices so as to implant the graft into the vessel.

Figure 16:
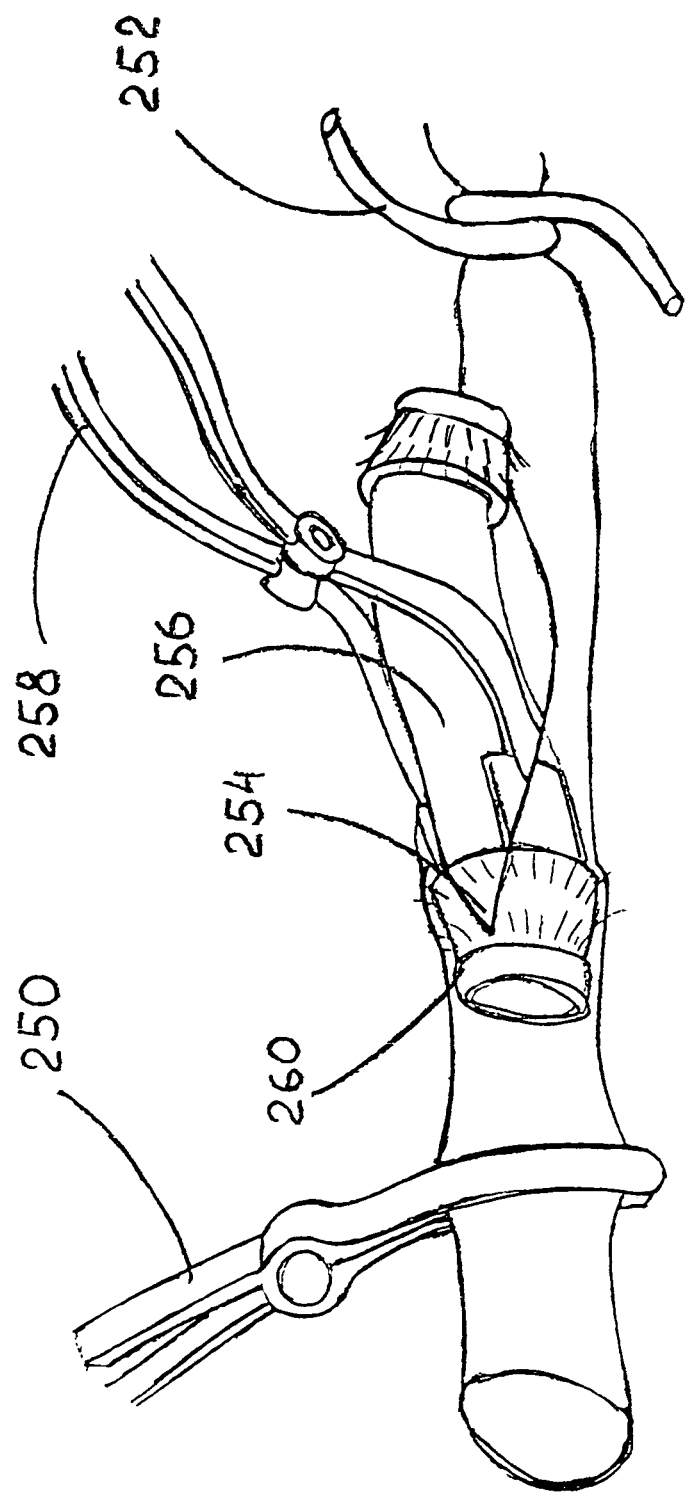
FIG. 16 illustrates an isometric view of graft positioning using forceps adapted for outer grasping in accordance with a preferred embodiment of the present invention.

Reference is now made to FIG. 16 illustrating an isometric view of graft positioning using forceps in accordance with a preferred embodiment of the present invention. Similarly to the previous procedure, blood is stopped using vascular clamp 250. A clip 252 is also put on the distal side of the vessel. An incision 254 is performed in the aneurysm and a graft 256 is positioned within the proximal portion of the vessel using a forceps 258 with jaws. Graft 256 is held and positioned within the vessel using forceps 258 having its jaws inserted between docking head 260 conic structure and the graft itself so as to gain control on the positioning of the graft's proximal side. The proximal docking head 260 is placed and nailed to the vessel's proximal portion. Forceps 258 are removed from the proximal portion of the vessel and then can be used in order to connect the distal side of the graft.

Figure 17:
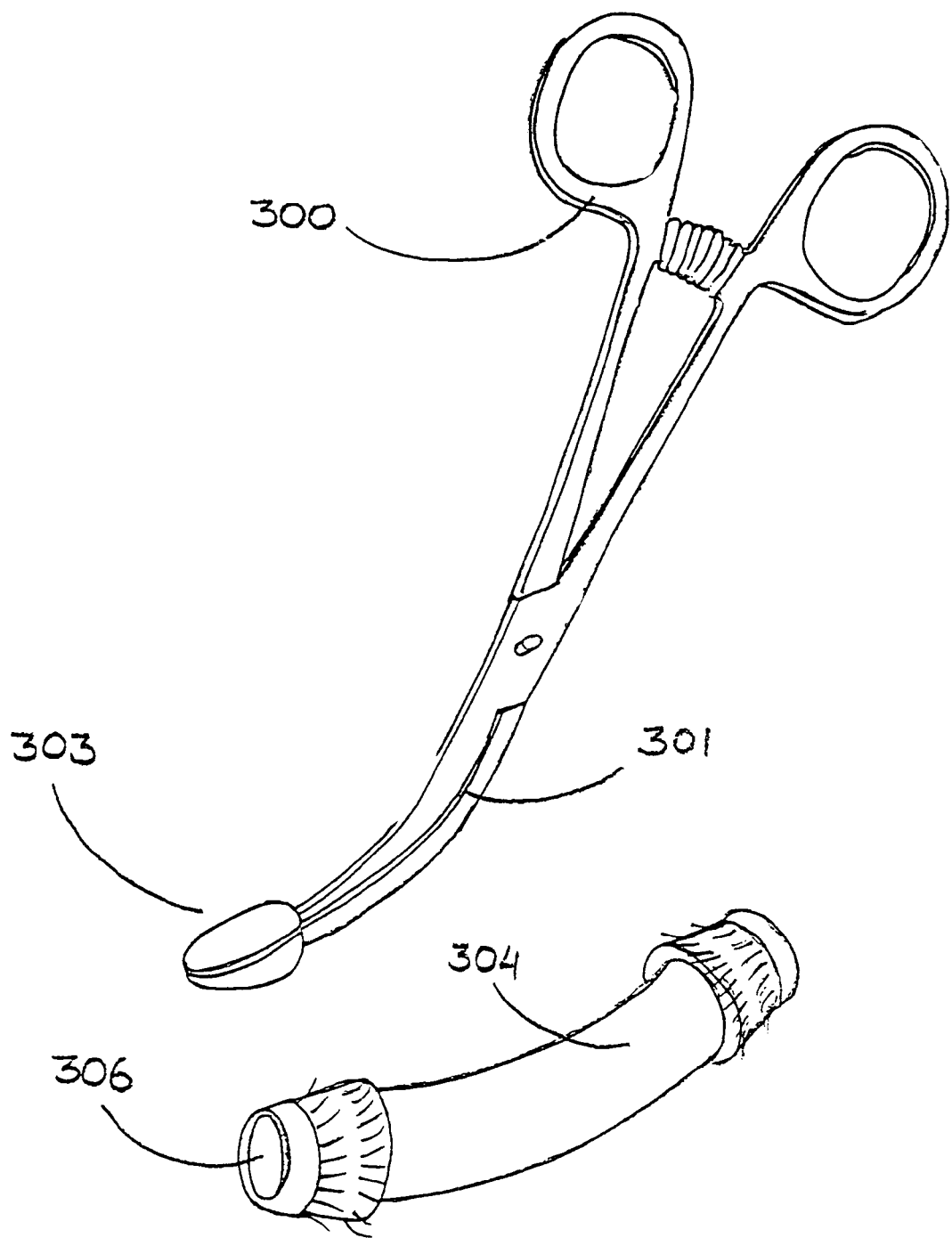
FIG. 17 illustrates an isometric view of forceps adapted for inner catching of a graft fastener in accordance with another preferred embodiment of the present invention.

Reference is now made to FIG. 17 illustrating an isometric view of forceps adapted for inner catching of a graft in accordance with another preferred embodiment of the present invention. Forceps 300 are designed with jaws 302 that are adapted to guide a graft 304 into the vessel. Jaws 302 have an elongated and curved body 301 and rounded and pointed head 303 at its edge. Elongated and curved body 301 is adapted to be threaded within graft 304 and rounded and pointed head 303 is designed to accord the inner diameter and shape of the edge 306 of graft 304.

Figure 18:
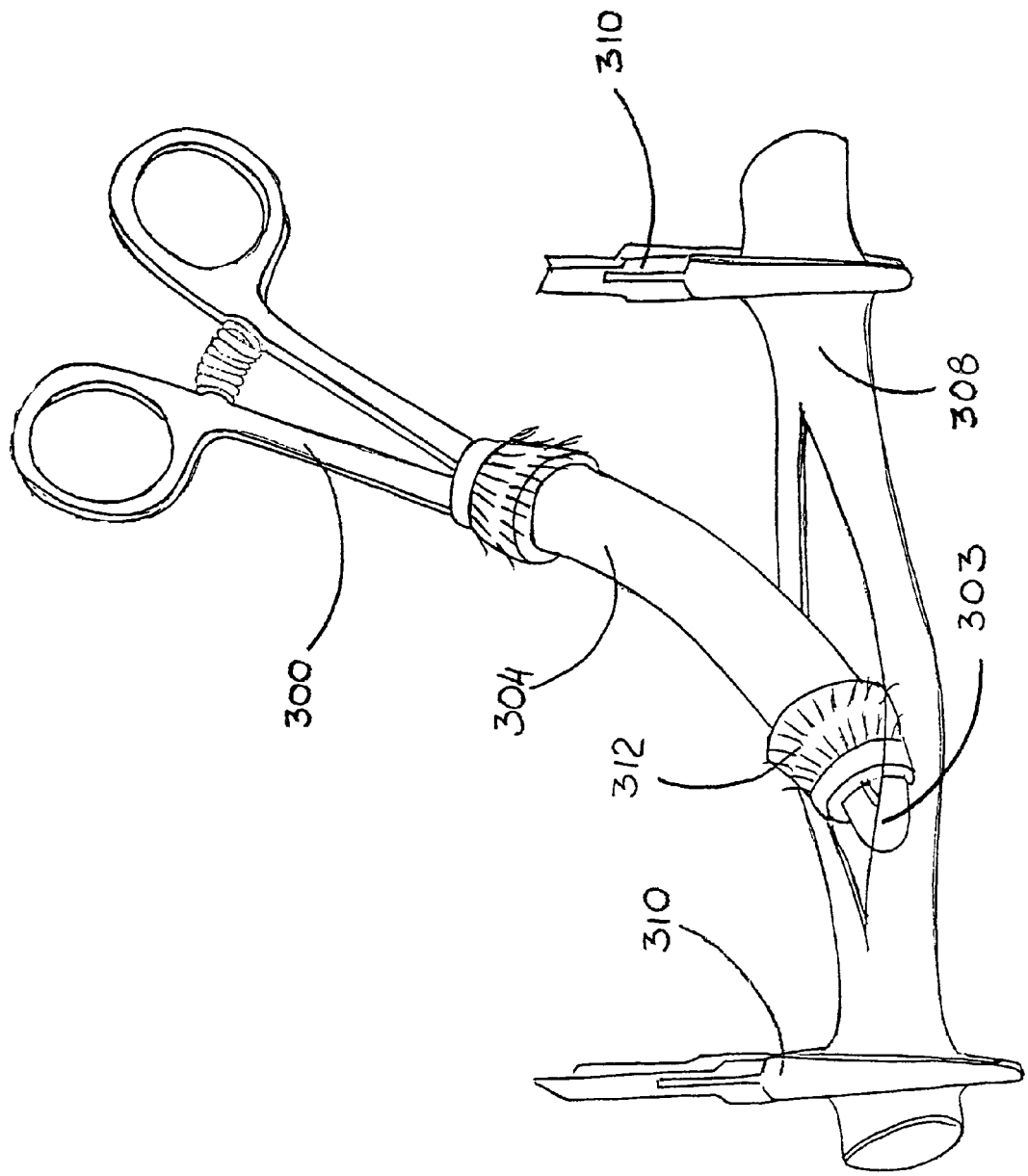
FIG. 18 illustrates the insertion of the graft to the vessel using forceps shown in FIG. 17.

Reference is now made to FIG. 18 illustrating the insertion of the graft to the vessel using forceps shown in FIG. 17. Vessel 308 is clipped by clips 310 as described herein before, proximally of an aneurysm and distally of it. An incision is made so as to insert the graft. Graft 304 is mounted onto jaws 302 while rounded head 303 partially protrudes beyond the graft, guiding the way to the proximal portion of the vessel 308. Using forceps 300, the surgeon directs docking head 312 into the healthy proximal portion of vessel 308 and couples it in the method described herein before. Then, the distal side can be coupled in the same manner.

It should be clear that the description of the embodiments and attached Figures set forth in this specification serves only for a better understanding of the invention, without limiting its scope as covered by the following claims.

It should also be clear that a person skilled in the art, after reading the present specification can make adjustments or amendments to the attached Figures and above described embodiments that would still be covered by the following claims.

The invention claimed is:

1. A vascular device to be prepared prior to insertion into a vessel with an aneurysm comprising:
   a tubular stentless vascular graft having a proximal portion, a distal portion, and an outer surface having a diameter;
   a first docking head for positioning at the distal portion of the graft and consisting essentially of a thin-walled truncated cone having a lumen therethrough wherein the lumen of the first docking head has a diameter that corresponds to the diameter of the outer surface of the graft; and
   a second docking head for positioning at the proximal end of the graft and consisting essentially of a thin-walled truncated cone having a lumen therethrough wherein the lumen of the second docking head has a diameter that corresponds to the diameter of the outer surface of the graft,
   wherein each of the docking heads is adapted for insertion into a vessel to create a seal with a vessel wall without requiring expansion,
   wherein each of the docking heads has a portion and an exterior surface of the portion has a plurality of outwardly pointing flexible barbs that are inclined towards a longitudinal direction of the graft at a predetermined angle,
   wherein each of the first and second docking heads is adapted to be adjusted along and fastened to the graft at a suitable position on the outer surface of the graft to form the vascular device, prior to insertion into the vessel, and
   wherein distal and proximal portions of the vascular device are capable of being coupled within the vessel distally and proximally, respectively, substantially to healthy portions of the aneurysm in a suture-less and rapid manner.

2. The vascular device of claim 1, wherein at least one of the docking heads is adapted to be fastened to the graft at a suitable position by a fastener selected from the group consisting of fit, glue, sutures, clips, and staples or by everting.

3. The vascular device of claim 1, wherein each of the docking heads has an outer diameter to couple the graft to the vessel and an inner lumen that has a diameter that corresponds to an outer diameter of the graft.

4. The vascular device of claim 1, a portion of each thin-walled truncated cone is provided with slits causing flexibility to said portion of the thin-walled truncated cone.

5. The vascular device of claim 1, wherein each thin-walled truncated cone has a concave, convex, or straight profile that corresponds to a profile of the graft.

6. The vascular device of claim 1, wherein an outer diameter of the thin-walled truncated cones are substantially smaller than an internal diameter of the vessel to guide a portion of the device into the vessel.

7. The vascular device of claim 1, wherein an outer diameter of the thin-walled truncated cones are substantially larger than a diameter of the vessel to assure firm sealing of the vessel.

8. The vascular device of claim 1, wherein some of the plurality of barbs have a length sized to a thickness of a wall of the vessel to enable perforating internal layers of the vessel wall.

9. The vascular device of claim 1, wherein some of the plurality of barbs are bent to establish a concave profile as compared to a radial cross-section of the thin-walled truncated cones.

10. The vascular device of claim 1, wherein some of the plurality of barbs are bent to establish a convex profile as compared to a radial cross-section of the thin-walled truncated cones.

11. The vascular device of claim 1, wherein a guiding end of the graft is adapted to be outwardly everted over a thin-walled truncated cone.

12. The vascular device of claim 1, wherein each docking head and the graft can each be selected according to individual vessel anatomy prior to assembly and insertion of the vascular device into the vessel.

13. The vascular device of claim 12, wherein each docking head and the graft are separate modules.

14. A vascular device for to be prepared prior to insertion into a vessel with an aneurysm, comprising:
    a bifurcated tubular stentless vascular graft having a distal portion having an outer surface with a diameter and a proximal portion having two tubular members each having an outer surface with a diameter;
    a first docking head for positioning at the distal portion of the graft and consisting essentially of a thin-walled truncated cone having a lumen therethrough wherein the lumen of the first docking head has a diameter that corresponds to the diameter of the outer surface of the graft; and
    second and third docking heads for positioning at the proximal portion of the graft and each consisting essentially of a thin-walled truncated cone having a lumen therethrough wherein the lumen of each of the second and third docking heads has a diameter that corresponds to the diameter of the outer surface of a tubular member,
    wherein each of the docking heads is adapted for insertion into a vessel to create a seal with a vessel wall without requiring expansion,
    wherein each of the docking heads has a portion and an exterior surface of the portion has a plurality of outwardly pointing flexible barbs that are inclined towards a longitudinal direction of the graft at a predetermined angle,
    wherein each of the docking heads is adapted to be adjusted along and fastened to the graft at a suitable position on the outer surface of the graft to form the vascular device prior to insertion into the vessel, and
    wherein distal and proximal portions of the vascular device are capable of being coupled within the vessel distally and proximally, respectively, substantially to healthy portions of the aneurysm in a suture-less and rapid manner.

15. The vascular device of claim 14, wherein at least one of the docking heads is adapted to be fastened to the graft at a suitable position by a fastener selected from the group consisting of fit, glue, sutures, clips, and staples or by everting.

16. The vascular device of claim 14, wherein each of the docking heads has an outer diameter to couple the graft to the vessel and an inner lumen that has a diameter that corresponds to an outer diameter of the graft.

17. The vascular device of claim 14, wherein said at least a portion of each thin-walled truncated cone is provided with slits causing flexibility to at least a portion of the thin-walled truncated cone.

18. The vascular device of claim 14, wherein each thin-walled truncated cone has a concave, convex, or straight profile that corresponds to a profile of the graft.

19. The vascular device of claim 14, wherein an outer diameter of the thin-walled truncated cones are substantially smaller than an internal diameter of the vessel to guide a portion of the device into the vessel.

20. The vascular device of claim 14, wherein an outer diameter of the thin-walled truncated cones are substantially larger than a diameter of the vessel to assure firm sealing of the vessel.

21. The vascular device of claim 14, wherein some of the plurality of barbs have a length sized to a thickness of a wall of the vessel to enable perforating internal layers of the vessel wall.

22. The vascular device of claim 14, wherein some of the plurality of barbs are bent to establish a concave profile as compared to a radial cross-section of the thin-walled truncated cones.

23. The vascular device of claim 14, wherein some of the plurality of barbs are bent to establish a convex profile as compared to a radial cross-section of the thin-walled truncated cones.

24. The vascular device of claim 14, wherein the thin-walled truncated cones are inwardly inverted, transitioning to the graft inwardly everted over a guiding end of the graft.

25. The vascular device of claim 14, wherein each docking head and the graft are adapted to be separate modules that can each be selected according to individual vessel anatomy prior to assembly and insertion of the vascular device into the vessel.

26. A vascular device to be prepared prior to insertion into a vessel with an aneurysm comprising:
    a tubular stentless vascular graft having a proximal portion, a distal portion, and an outer surface having a diameter;
    a first stentless docking head for positioning at the distal portion of the graft and consisting essentially of a thin-walled truncated cone having a lumen therethrough wherein the lumen of the first docking head has a diameter that corresponds to the diameter of the outer surface of the graft; and
    a second stentless docking head for positioning at the proximal end of the graft and consisting essentially of a thin-walled truncated cone having a lumen therethrough wherein the lumen of the second docking head has a diameter that corresponds to the diameter of the outer surface of the graft,
    wherein each of the docking heads is adapted for insertion into a vessel to create a seal with a vessel wall without requiring expansion,
    wherein each of the docking heads has a portion and an exterior surface of the portion has a plurality of outwardly pointing flexible barbs that are inclined towards a longitudinal direction of the graft at a predetermined angle,
    wherein each of the first and second docking heads is adapted to be adjusted along and fastened to the graft at a suitable position on the outer surface of the graft to form the vascular device, prior to insertion into the vessel, and
    wherein distal and proximal portions of the vascular device are capable of being coupled within the vessel distally and proximally, respectively, substantially to healthy portions of the aneurysm in a suture-less and rapid manner.

27. A vascular device for to be prepared prior to insertion into a vessel with an aneurysm, comprising:
    a bifurcated tubular stentless vascular graft having a distal portion having an outer surface with a diameter and a proximal portion having two tubular members each having an outer surface with a diameter;

a first stentless docking head for positioning at the distal portion of the graft and consisting essentially of a thin-walled truncated cone having a lumen therethrough wherein the lumen of the first docking head has a diameter that corresponds to the diameter of the outer surface of the graft; and second and third stentless docking heads for positioning at the proximal portion of the graft and each consisting essentially of a thin-walled truncated cone having a lumen therethrough wherein the lumen of each of the second and third docking heads has a diameter that corresponds to the diameter of the outer surface of a tubular member, wherein each of the docking heads is adapted for insertion into a vessel to create a seal with a vessel wall without requiring expansion, wherein each of the docking heads has a portion and an exterior surface of the portion has a plurality of outwardly pointing flexible barbs that are inclined towards a longitudinal direction of the graft at a predetermined angle, wherein each of the docking heads is adapted to be adjusted along and fastened to the graft at a suitable position on the outer surface of the graft to form the vascular device prior to insertion into the vessel, and wherein distal and proximal portions of the vascular device are capable of being coupled within the vessel distally and proximally, respectively, substantially to healthy portions of the aneurysm in a suture-less and rapid manner.

* * * * *